(12) United States Patent
Chen et al.

(10) Patent No.: US 11,059,855 B2
(45) Date of Patent: Jul. 13, 2021

(54) ANTIMICROBIAL PEPTIDES AND METHODS OF MAKING AND USING SAME

(71) Applicant: THE JOHNS HOPKINS UNIVERSITY, Baltimore, MD (US)

(72) Inventors: Charles H. Chen, Baltimore, MD (US); Martin B. Ulmschneider, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/492,248

(22) PCT Filed: Mar. 12, 2018

(86) PCT No.: PCT/US2018/021985
§ 371 (c)(1),
(2) Date: Sep. 9, 2019

(87) PCT Pub. No.: WO2018/165655
PCT Pub. Date: Sep. 13, 2018

(65) Prior Publication Data
US 2020/0048303 A1 Feb. 13, 2020

Related U.S. Application Data

(60) Provisional application No. 62/469,588, filed on Mar. 10, 2017.

(51) Int. Cl.
| | | |
|---|---|---|
| *C07K 1/04* | (2006.01) | |
| *A61P 31/04* | (2006.01) | |
| *G16B 30/10* | (2019.01) | |
| *G16B 30/20* | (2019.01) | |
| *A01N 43/50* | (2006.01) | |
| *C07K 7/08* | (2006.01) | |
| *C12N 15/10* | (2006.01) | |
| *A61K 38/00* | (2006.01) | |

(52) U.S. Cl.
CPC .............. *C07K 1/047* (2013.01); *A01N 43/50* (2013.01); *A61P 31/04* (2018.01); *C07K 7/08* (2013.01); *C12N 15/1089* (2013.01); *G16B 30/10* (2019.02); *G16B 30/20* (2019.02); *A61K 38/00* (2013.01)

(58) Field of Classification Search
CPC .................. C07K 1/047; A61P 31/04
See application file for complete search history.

(56) References Cited

U.S. PATENT DOCUMENTS

| | | | | |
|---|---|---|---|---|
| 8,084,399 | B2* | 12/2011 | Yu ............................ | C07K 7/08 506/9 |
| 8,142,764 | B2* | 3/2012 | Demuth .................. | A61K 8/64 424/49 |
| 10,022,425 | B2* | 7/2018 | Bancel ............... | A61K 38/1729 |
| 10,258,697 | B2* | 4/2019 | Chen .................. | A61K 47/6911 |
| 2003/0233675 | A1* | 12/2003 | Cao ....................... | C07K 14/195 800/279 |
| 2009/0214603 | A1* | 8/2009 | Demuth ................. | A23L 33/18 424/400 |
| 2017/0065675 | A1* | 3/2017 | Bancel ............... | A61K 38/1729 |
| 2017/0340754 | A1* | 11/2017 | Chen ..................... | C12N 15/11 |

FOREIGN PATENT DOCUMENTS

WO    WO 2016/069912    *    5/2016    ............. A61K 38/46

OTHER PUBLICATIONS

Leman, J., et al., "Computational modeling of membrane proteins" Proteins. Jan. 2015 ; 83(1): 1-24. doi:10.1002/prot.24703.
Rausch, J., "Rational combinatorial design of pore-forming beta-sheet peptides" PNAS, Jul. 26, 2005, vol. 102, No. 30, pp. 10511-10515.
Zasloff, Magainins, a class of antimicrobial peptides from Xenopus skin: isolation, characterization of two active forms, and partial cDNA sequence of a precursor. (1987) Proceedings of the National Academy of Sciences of the United States of America, 84(15), 5449-5453.
Lehrer et al., Interaction of human defensins with *Escherichia coli*. Mechanism of bactericidal activity. (1989) Journal of Clinical Investigation, 84(2), 553-561.
Yeaman et al., Mechanisms of antimicrobial peptide action andresistance. (2003) Pharmacological Reviews, 55(1), 27-55.
Wiedman et al., Highly efficient macromolecule-sized poration of lipid bilayers by a synthetically evolved peptide. (2014) Journal of the American Chemical Society, 136(12), 4724-4731.
Krauson, He et al., Gain-of-function analogues of the pore-forming peptide melittin selected by orthogonal high-throughput screening. (2012) Journal of the American Chemical Society, 134(30), 12732-12741.
Krauson, Hall et al., Conformational fine-tuning of pore-forming peptide potency and selectivity. (2015) Journal of the American Chemical Society, 137(51), 16144-16152.
Wiedman, Wimley, et al., Testing the limits of rational design by engineering pH sensitivity into membrane-active peptides. (2015) Biochimica et Biophysica Acta, 1848(4), 951-957.
Wiedman, Kim, et al., (2017) pH-triggered, macromolecule-sized poration of lipid bilayers by synthetically evolved peptides. Journal of the American Chemical Society, 139(2), 937-945.
Sreedharan et al., TDP-43 mutations in familial and sporadic amyotrophic lateral sclerosis.(2008) Science, 319 (5870), 1668-1672.

(Continued)

*Primary Examiner* — Amber D Steele
(74) *Attorney, Agent, or Firm* — MH2 Technology Law Group LLP

(57) ABSTRACT

The present invention provides a new methodology combining MD simulations and database-guided high-throughput screening to rationally design pore forming membrane-active peptides. The present inventive methodology is able to allow tuning of a range of structural and functional properties such as pore size and selectively targeting membranes with specific lipid compositions. The present inventive methods will ultimately allow de novo design of membrane-active peptides for a wide range of biomedical applications, including for example, antimicrobial agents.

8 Claims, 16 Drawing Sheets
Specification includes a Sequence Listing.

(56) References Cited

OTHER PUBLICATIONS

Chen et al., Induction of amyloid fibrils by the C-terminal fragments of TDP-43 in amyotrophic lateral sclerosis. (2010) Journal of the American Chemical Society, 132(4), 1186-1187.
Liu et al., Delineating the membrane-disrupting and seeding properties of the TDP-43 amyloidogenic core. (2013) Chemical Communications, 49(95), 11212-11214.
Sun et al., The influence of pathological mutations and proline substitutions in TDP-43 glycine-rich peptides on its amyloid properties and cellular toxicity. (2014) PloS One. 9(8), e103644.
Grau-Campistany et al., Hydrophobic mismatch demonstrated for membranolytic peptides, and their use as molecular rulers to measure bilayer thickness in native cells. (2015) Scientific Reports, 5, 9388.
Grau-Campistany, Strandberg, Extending the hydrophobic mismatch concept to amphiphilic membranolytic peptides. (2016) Journal of Physical Chemistry Letters, 7(7), 1116-1120.
Leveritt et al., The structure of a melittin-stabilized pore. (2015) Biophysical Journal, 108(10), 2424-2426.
Perrin, Fu et al., Simulations of Membrane-Disrupting Peptides II: AMP Piscidin 1 Favors Surface Defects over Pores. (2016) Biophysical Journal, 111(6), 1258-1266.
Wang et al., Spontaneous formation of structurally diverse membrane channel architectures from a single antimicrobial peptide. (2016) Nature Communications, 7, 13535.
Ulmschneider et al., Spontaneous transmembrane helix insertion thermodynamically mimics translocon-guided insertion. (2014) Nature Communications, 5, 4863.
Mishra et al., Ab initio design of potent anti-MRSA peptides based on database filtering technology. (2012) Journal of the American Chemical Society, 134 (30),12426-12429.
Ulmschneider, M.B., Ulmschneider, J.P. Folding peptides into lipid bilayer membranes. (2008) Journal of Chemical Theory and Computation, 4(11), 1807-1809.
Ulmschneider, J. P., et al., In silico partitioning and transmembrane insertion of hydrophobic peptides under equilibrium conditions. (2011) Journal of the American Chemical Society, 133(39), 15487-15495.
Chen, Wiedman et al., Absorption and folding of melittin onto lipid bilayer membranes via unbiased atomic detail microsecond molecular dynamics simulation. (2014) Biochimica et Biophysica Acta, 1838(9), 2243-2249.
Wang, Li et al., APD3: the antimicrobial peptide database as a tool for research and education. (2015) Nucleic Acids Research, 44 (D1), D1087-D1093.
Peng et al., Five different piscidins from Nile Tilapia, *Oreochromis niloticus*: analysis of their expressions and biological functions. (2012) PLoS One, 7(11): e50263.
Wu et al., Proteomic analysis of skin defensive factors of tree frog *Hyla simplex*. (2011) Journal of Proteome Research, 10(9): 4230-4240.
Dempsey et al., Contribution of proline-14 to the structure and actions of melittin. (1991) FEBS Letters, 281(1-2), 240-244.
Rex, A Pro → Ala substitution in melittin affects self-association, membrane binding and pore-formation kinetics due to changes in structural and electrostatic properties. (2000) Biophys. Chem., 85(2-3), 209-228.
Fernandez et al., Proline facilitates membrane insertion of the antimicrobial peptide maculatin 1.1 via surface indentation and subsequent lipid disordering. (2013) Biophysical Journal, 104(7), 1495-1507.
Sani et al., Proline-15 creates an amphipathic wedge in maculatin 1.1 peptides that drives lipid membrane disruption. (2015) Biochimica et Biophysica Acta, 1848(10):2277-2289.
Chen, C.H., et al., Mechanisms of membrane pore formation by amyloidogenic peptides in amyotrophic lateral sclerosis, Chem. Eur. J. 2016; 22(29):9958-9961.
Perrin, S.B. & Pastor, R.W., Simulations of Membrane-Disrupting Peptides I: Alamethicin Pore Stability and Spontaneous Insertion, Biophysical Journal 2016; 111(6):1248-1257.

\* cited by examiner

TIMESCALE (μs)

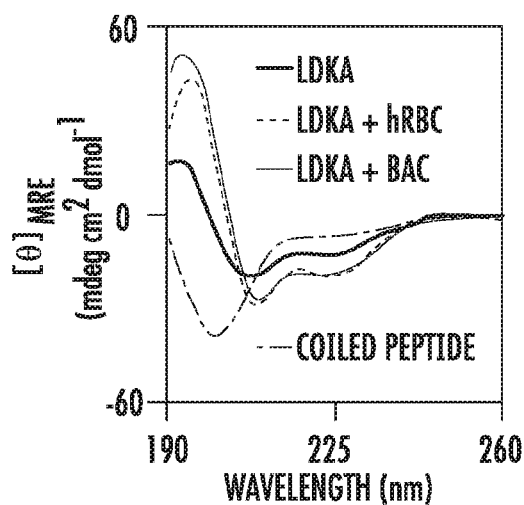
FIG. 3A
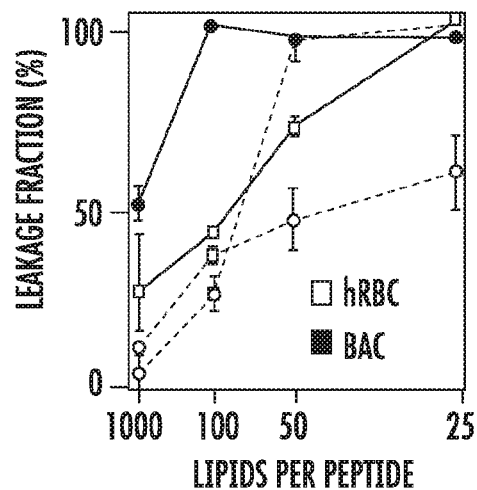
FIG. 3B
| MINIMUM INHIBITORY CONCENTRATION (MIC) | | |
|---|---|---|
| E. COLI ATCC 25922 | E. AUREUS ATCC 27853 | E. AERUGINOSA PA01 |
| 35±9 μM | 10±1 μM | 66±14 μM |
FIG. 3C
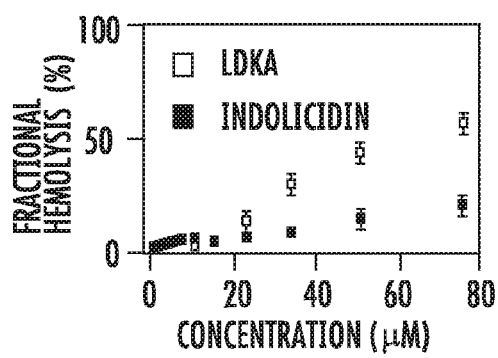
FIG. 3D

ANTIMICROBIAL PEPTIDES AND METHODS OF MAKING AND USING SAME

CROSS-REFERENCE TO RELATED APPLICATIONS

This application is a 35 U.S.C. § 371 U.S. national entry of International Application PCT/US2018/021985, having an international filing date of Mar. 12, 2018, which claims the benefit of U.S. Provisional Application No. 62/469,588, filed Mar. 10, 2017, the content of each of the aforementioned applications is herein incorporated by reference in their entirety.

INCORPORATION-BY-REFERENCE OF MATERIAL SUBMITTED ELECTRONICALLY

This application contains a sequence listing, which has been submitted electronically in ASCII format via EFS-Web and is hereby incorporated by reference in its entirety. Said ASCII copy created 16 Feb. 2021, is named 0184.0128-US ST25 and is 8,177 bytes in size.

BACKGROUND OF THE INVENTION

Pore-forming, membrane-active antimicrobial peptides (AMPs) are powerful and ubiquitous components of the innate immune defence in all domains of life. AMPs are amphiphilic peptides that selectively target and kill a wide variety of microbial pathogens at low micro-molar concentrations.[1-3]

Despite the discovery of thousands of AMPs over the last 20 years,[3, 4] the molecular mechanisms driving antimicrobial activity remain poorly understood. Known AMPs vary widely in size, sequence and secondary structure, and no common activity motif has been discovered to date. This lack of sequence-function relationship is unusual for proteins and has hindered efforts aimed at understanding the root causes of AMP activity. For example, a few amino acid mutations in melittin can result in dramatic changes of pore stability,[5] potency,[6,7] and selectivity for particular membrane types.[7] In addition, Wiedman et al. showed few amino acid substitutions of Melp5, a gain of function melittin variant, can alter membrane poration ability by only disrupting liposomes in acidic pH conditions.[8,9] In nature, minor changes of a membrane-active peptide (MAP) sequence can increase the potency of membrane disruption and further induce protein-misfolding diseases. A typical example is the neurodegenerative peptide: TDP-43 C-terminal fragments.[10-14] Peptide length also acts as an important factor. Ulrich et al. reported several rationally designed helical peptides with repeated "KIAGKIA" (SEQ ID NO: 25) motifs with peptide length between 14 and 28 amino acids, and they validated that the peptide length can affect its ability to damage cell membranes[15] and penetrate into the membrane.[16]

This presents a significant challenge for rational de novo design of AMPs. At present, helical AMPs are typically developed using helical wheel projections, assuming simple parallel channel structures. Channels are designed by empirical modification of peptide amphiphilicity and variation of the non-polar and polar faces of the helix using peptide libraries. Subsequent high-throughput screening is used to select functional sequences; however, the structure and function of AMPs in fluid membranes are dynamic and transient, and a single peptide sequence can result in several different oligomeric structures, that can deviate significantly from simple symmetric helical assemblies.[17] This suggest that successful rational design of AMPs requires knowledge of the dynamic structural ensemble in the membrane, rather than a simple static structural model.

SUMMARY OF THE INVENTION

Here, the inventors provide a new methodology that uses unbiased atomic detail folding partitioning MD simulations to guide the rational, de novo design of synthetic, pore-forming, membrane-active peptides (MAPs) which have antimicrobial peptide (AMP) activity. Starting from a simple polyleucine sequence we show that this iterative approach allows us to refine dynamic structural and functional properties resulting in a powerful pore-forming AMP.

The present inventive methodology is able to allow tuning of a range of structural and functional properties such as pore size and selectively targeting membranes with specific lipid compositions. The present inventive methods will ultimately allow de novo design of MAPs for a wide range of biomedical applications.

In accordance with some embodiments, the present invention provides the use of MD simulations to study the mechanisms of AMP folding and pore assembly in a bacterial model membrane. The atomic detail information of how pores form from the MD simulation was used to develop a novel AMP which we call "LDKA" (SEQ ID NO: 3, Table 1), which is a template sequence based on atomic detail structural information from the MD simulations. This simple peptide is composed a small number of amino acids and shows powerful pore-forming properties. A statistical analysis of several thousand AMPs from a first AMP library was then used to optimize the LDKA template sequence, followed by testing the peptides in the second generated library with a high-throughput screen using dye leakage assays to both bacterial and mammalian membrane model vesicles used to screen the potent peptides that have significant selectivity to target the cells. The information from this step allowed the inventors to fine-tune the pore size and the binding selectivity for different membrane types. LDKA exhibits high antimicrobial activity and forms pores in both charged (POPG) and neutral (POPC) lipid vesicles.

TABLE 1

Sequences of polyleucine-based membrane-active peptides

| SEQ ID NO | Name | Sequence |
|---|---|---|
| 1 | $GL_5KL_6G$ | GLLLLLKLLLLLLG-COOH |
| 2 | LDKL | GLLDLLKLLLLKLLG-COOH |
| 3 | LDKA | GLLDLLKLLLKAAG-COOH |
| 4 | K7H | GLLDLLHLLLKAAG-AMIDE |
| 5 | 7F3 | GLADLAKLLLKLLGW-AMIDE |
| 6 | 28H6 | GLLDLLKLLLKLAGW-AMIDE |
| 7 | 25B2 | GLDDLAKLLLKLAGW-AMIDE |
| 8 | 4H9 | GLDDLLKALLKAAGW-AMIDE |
| 9 | 7D12 | GLLDDAKLLAKLAGW-AMIDE |

TABLE 1-continued

Sequences of polyleucine-based membrane-active peptides

| SEQ ID NO | Name | Sequence |
|---|---|---|
| 10 | 7G6 | GLLDLPKALAKALGW-AMIDE |
| 11 | 11D12 | GLADAAKLLLKAAGW-AMIDE |
| 12 | 24F1 | GLLDAAKLLAKAAGW-AMIDE |

The present inventors also provide mutations of the LDKA sequence template which can introduce preferential binding and pore formation in charged and neutral lipid bilayers and investigate specific binding to either lipid type correlates to activity for human versus bacterial cells. The inventors show that simple mutations can modulate the size of the pores formed by this peptide, as well as the induced preferential pore-forming potency in charged versus neutral lipid bilayers. The inventors further show that these properties are well correlated with antimicrobial activity for specific bacteria and selectivity for bacteria over human red blood cells.

In accordance with an embodiment, the present invention provides a method for designing pore forming, membrane-active peptides comprising the steps of: a) providing a first template membrane-active peptide; b) comparing the amino acid sequence of the first template peptide to the amino acid sequences of known membrane-active peptides located in a first membrane-active peptide database; c) identifying similarities in hydrophobicity and amino acid sequence motif between the first template peptide and the known membrane-active peptides; d) identifying amino acid locations in the first template peptide which can modified using the information from c); e) generating a plurality of modified membrane-active peptide sequences using the information from d); 0 performing MD simulations on the plurality of modified membrane-active peptide sequences and determining whether the plurality of modified membrane-active peptide sequences have the physical characteristics of self-assembly into a pore-forming structure; g) synthesizing the plurality of modified membrane-active peptide sequences of e); h) testing the plurality of modified membrane-active peptides in an in vitro cell membrane testing system to determine efficacy of pore formation in cell membranes; and i) identifying one or more modified membrane-active peptides when the membrane testing system gives a positive antimicrobial result.

In some embodiments, the above method is then used to create a library of positive modified antimicrobial peptides, which then are further analyzed with database guided high-throughput screening.

In accordance with another embodiment, the present invention provides a novel pore forming antimicrobial peptide termed "LDKA" having the amino acid sequence GLLDLLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLD-DAKLLAKLAGW-AMIDE (7D12; SEQ ID NO: 9, Table 1), GLLDLPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) or a functional homolog of or functional fragment thereof; or a fusion polypeptide comprising an amino acid sequence of any of the above peptides.

In accordance with a further embodiment, the present invention provides a method of treating a microbial infection in a subject in need thereof comprising administering to the subject an effective amount of one or more antimicrobial peptides selected from the group consisting of GLLD-LLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAK-LAGW-AMIDE (7D12; SEQ ID NO: 9, Table 1), GLLD-LPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides.

In accordance with a still another embodiment, the present invention provides a method of treating a microbial infection in a subject in need thereof comprising administering to the subject an effective amount of a pharmaceutical composition comprising one or more antimicrobial peptides selected from the group consisting of GLLDLLKLLL-KAAG-COOH (LDKA; SEQ ID NO: 3, Table 1), GLLD-LLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKA-LAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides, and a pharmaceutically acceptable carrier.

In accordance with a further embodiment, the present invention provides a method of treating a microbial infection in a subject in need thereof comprising administering to the subject an effective amount of a pharmaceutical composition comprising one or more antimicrobial peptides selected from the group consisting of GLLDLLKLLLKAAG-COOH (LDKA; SEQ ID NO: 3, Table 1), GLLDLLHLLL-KAAGW-AMIDE (K7H; SEQ ID NO: 4, Table 1), GLAD-LAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKALAKALGW-AMIDE (7G6; SEQ ID NO: 10, Table 1), GLADAAKLLL-KAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides, at least one additional biologically active agent, and a pharmaceutically acceptable carrier.

In accordance with an embodiment, the present invention provides a method of treating a surface to prevent or remove microbial growth comprising applying to the surface an effective amount of one or more antimicrobial peptides selected from the group consisting of GLLDLLKLLL-KAAG-COOH (LDKA; SEQ ID NO: 3, Table 1), GLLD-LLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKA-LAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides.

BRIEF DESCRIPTION OF THE DRAWINGS

FIGS. 3A-3D In vitro experiments show LDKA is a helical membrane-active antimicrobial peptide. (3A) Circular dichroism spectra of 50 µM LDKA in buffer (black), LDKA in the presence of hRBC model vesicles (red, P:L=1: 12.5), and LDKA in the presence of bacterial (Bac) model vesicles (blue, P:L=1:12.5) in 10 mM phosphate buffer at pH 7. The peptide is partially helical in solution and folds onto both bilayer models. A coiled peptide spectra is shown for reference (grey). (3B) Dye leakage assay of LDKA with hRBC (blue) and Bac (red) model vesicles. Solid lines mean that ANTS/DPX (M.W.=400) is the trapped fluorescent marker in the vesicle, while dashed lines show data for trapped 10-kDa Dextran. (3C) Bacterial minimum inhibition concentration (MIC) shows LDKA is a powerful AMP. Initial bacterial cell density was prepared with ~3×10$^5$ CFU/mL. LDKA was co-incubated with the bacteria in Lysogeny broth at 37° C. for 12 hr. The wavelength of optical density was determined at 600 nm. (3D) Hemolysis assay of titrated LDKA with red blood cell. Indolicidin, an antimicrobial peptide that has 13 amino acids with coiled structure, was used as a reference.

DETAILED DESCRIPTION OF THE INVENTION

The present invention provides a new methodology combining MD simulations and database-guided high-throughput screening to rationally design membrane-active peptides. This inventive methodology is able to provide tuning of a range of structural and functional properties such as pore size and selectively targeting membranes with specific lipid compositions. This will ultimately allow de novo design of MAPs for a wide range of biomedical applications.

The present invention provides that unbiased atomic detail peptide folding-assembly simulations have become suitably powerful to guide the ab initio design of potent pore-forming membrane-active peptides, starting from a simple hydrophobic polyleucine template sequence. The inventive process arrives at a functional motif that occurs naturally in frog AMPs, and reveals how this sequence motif binds, folds, oligomerizes, and forms pores in bacterial model membranes. Both the pore-forming properties as well as antimicrobial activity of the inventive peptides were confirmed experimentally, validating the design methodology presented here. This opens the door to rational design and optimization of other membrane active peptides.

The inventive LDKA analogues reveal that a small number of relatively minor mutations (L to A) in the LDKA sequence can dramatically change the selectivity of the peptide for charged and neutral LUVs, and even have result in selectivity for different bacterial strains.

Figure 12A:
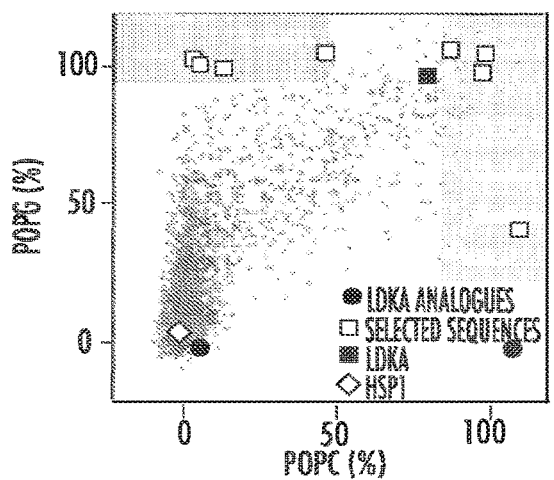
FIGS. 12A-12D Eight selected LDKA analogues and their in vitro hemolytic activity with red blood cell. (12A) Selected LDKA analogues from the high throughput screen. Yellow and red regions are the peptides that have general and cell-selective activity, respectively. (12B) The hemolytic activity with red blood cell varies with peptide concentration. Linear regression analysis of (12C) hemolysis (at 75 µM peptide concentration) and ANTS leakage fraction from POPC vesicle (at P:L=1:1000) and (12D) Hemolysis (at 75 µM peptide concentration) and peptide helicity in POPC (at P:L=1:12).
Figure 12B:
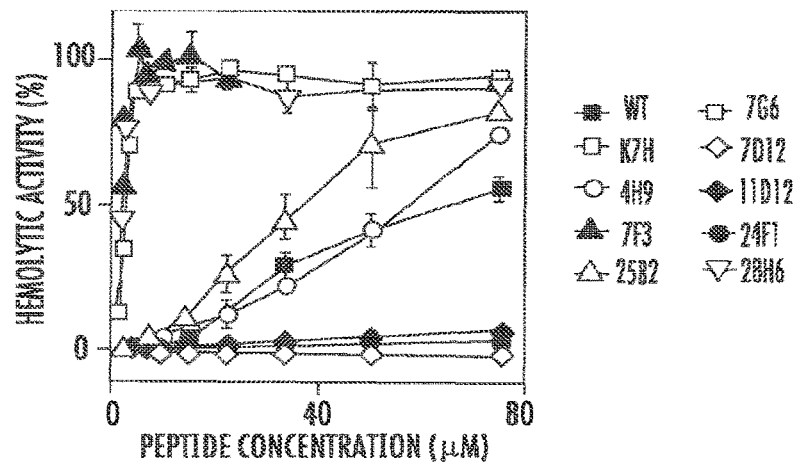
Figure 12C:
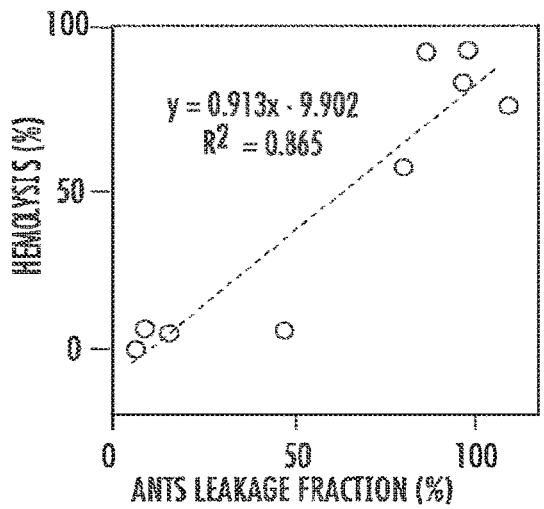
Figure 12D:
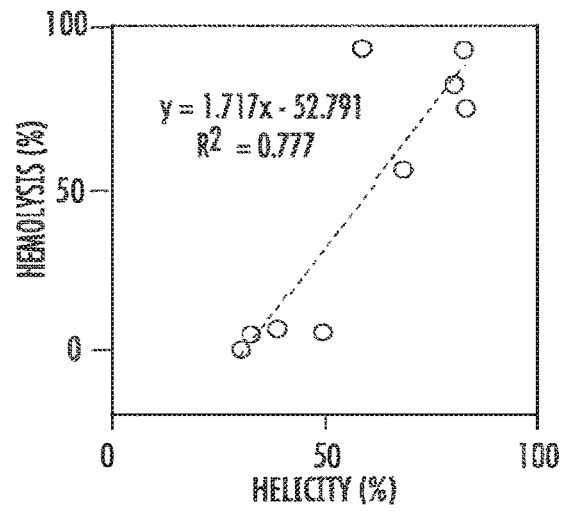
Figure 16A:
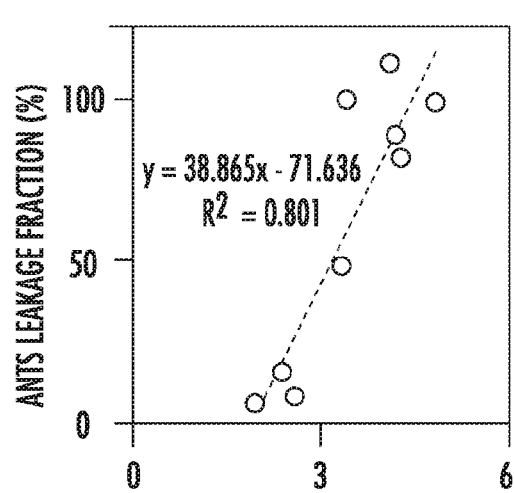
FIGS. 16A-16D Linear regression analysis of hydrophobic moment with several parameters, includes (16A) hydrophobic moment and fluorescent dye leakage fraction from POPC vesicle, (16B) hydrophobic moment and helical structure in phosphate buffer and with POPC vesicle, (16C) helicity at 95° C. and hydrophobic moment, and (16D), hydrophobic moment and hemolysis assay at 75 µM peptide concentration.
Figure 16B:
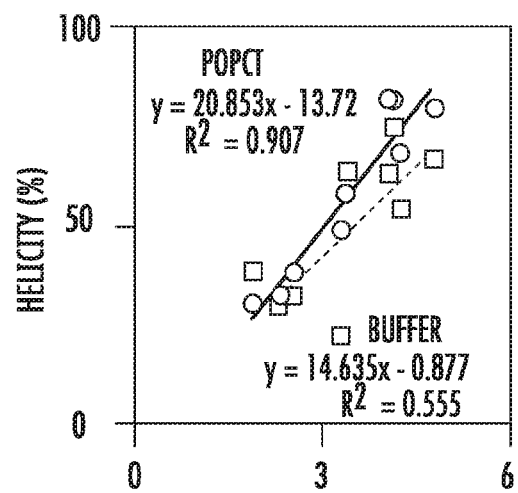
Figure 16C:
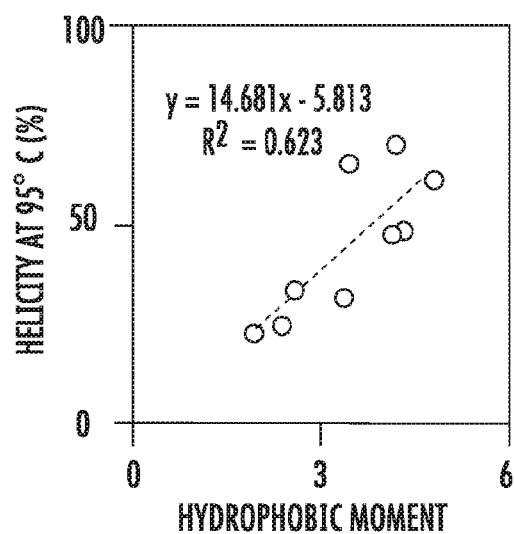
Figure 16D:
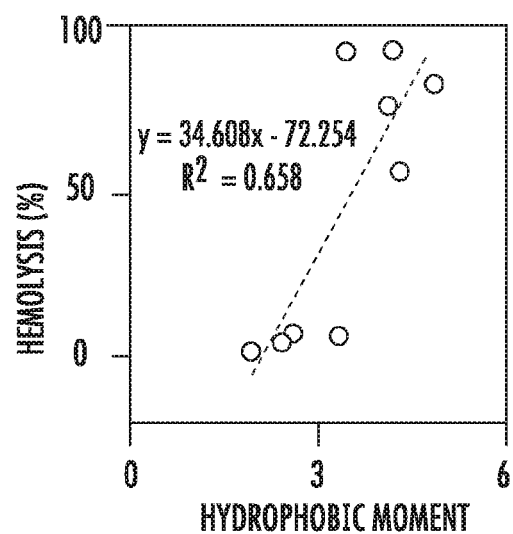

It was found that the hemolytic activity is linearly correlated to the hydrophobic moment with $R^2$=0.66 (FIG. 16d). Hydrophobic moment of membrane-selective peptides has values in the range of 1.9-3.3 and non-selective peptides have values between 3.4 and 4.8, except K7H, which has a low hydrophobic moment of 3.0, but is strongly haemolytic. This suggests that hydrophobic moment is not good enough to accurately predict cytotoxicity, and may requires a larger sample size to optimize the prediction. Instead, fluorescent dye leakage assays may be a good model to predict AMP hemolytic activity with red blood cells (FIG. 12a and FIG. 12b) and this activity is strongly linearly correlated with an R-squared value of 0.87 (FIG. 12c), and the R-squared value of helicity and hemolysis is 0.78 (FIG. 12d).

Eight out of ten LDKA peptides are able to inhibit the growth of E. coli with 19-57 µM peptide concentrations, except K7H, 28H6, and 7D12 that have no antibacterial activity against E. coli, even at high peptide concentration (75 µM). 7D12 has the lowest hydrophobic moment 1.92 that may not be potent enough to fold and penetrate into the membrane.

Although these peptides share similar sequence and similar structure, they result in different antibacterial activity. More specifically, only few peptides are active against S. aureus and only one peptide can inhibit the P. aeruginosa. Antibiotic-resistance is another serious threat. Half of the LDKA analogues that are able to inhibit S. aureus and fail against methicillin-resistant Staphylococcus aureus (MRSA) (Table 10). Although our LDKA analogues are less or not efficient against S. aureus and P. aeruginosa, many of them are effective against E. coli and some of them even do not harm the red blood cells. Therefore, we created four different drug-resistant E. coli strains that are strongly resistant to each four classic antibiotics: ceftazidime, ciprofloxacin, streptomycin, and gentamicin. The results reveal that membrane selective peptides work better than non-selective peptides against drug-resistant bacteria.

In accordance with the present invention, the peptide sequence was simplified using four different amino acids (Ala, Leu, Lys, and Asp) for a template sequence of GxxD$_4$xxK$_7$xxxK$_{11}$xxGW-Amide (SEQ ID NO: 24), where 'x' represents one of the four amino acids. Our result shows that the hemolytic activity and antibacterial activity against E. coli can be simply explained by fine-tuning peptide hydrophobicity. Other than fixed lysine on position 7 and 11, no additional lysine was observed in the analogues. Additional aspartic acids were observed on position 3 and 5, which is next to the fixed aspartic acid on position 4. The net charges of these analogues are between +1 and +2, and consistent with the net charge of +1 found in the majority of AMPs in the APD[4,18]. It shows that cationic residues can assist peptide binding onto anionic bacterial membranes; however, more cationic charges can result in lower hydrophobicity with higher energy barriers to cross the membranes.

As such, in accordance with an embodiment, the present invention provides a pore-forming, membrane-active peptide having the amino acid sequence of GxxD$_4$xxK$_7$xxxK$_{11}$xxGW-Amide (SEQ ID NO: 24), where 'x' is independently any one of the four amino acids (Ala, Leu, Lys, and Asp), with the proviso that the sequence cannot be SEQ ID NO: 12.

A good example is melittin (sequence: GIGAVLKVLTTGLPALISWIKRKRQQ-Amide (SEQ ID NO: 22), which is composed of 26 amino acids and has net charge of +6. It has four positive charges (—KRKR—) on its C-terminus, and its N-terminus is more hydrophobic (GIGAVLKVL-(SEQ ID NO: 23)). The hydrophobic moment of melittin is 3.9 and it is more hydrophobic than many LDKA analogues because it has much longer peptide length. Interestingly, melittin L16G mutant has membrane-selectivity to kill bacteria and has lower hemolytic activity against red blood cell[6]. It has comparatively lower hydrophobic moment of 3.5 than its wildtype.

In summary, the inventors used polyleucine-based AMP, LDKA, as the sequence template and applied database-guided high-throughput screening and found minor substitutions of the amino acids can dramatically change its secondary structure, potency, and membrane-selectivity. The inventors found several powerful antimicrobial peptides that have powerful cell selectivity to distinguish between mammalian cell and bacterial membrane, and even between different bacterial species. It shows that the LDKA analogues are effective to against E. coli biofilms and drug-resistant E. coli, and shows the inventive LDKA analogues can be applied for biosensor, antibiotics, and targeted drug delivery. Furthermore, small fluorescent dye leakage of POPC and POPG vesicles are good models to predict its hemolysis and antimicrobial activity against E. coli for high-throughput screening. This knowledge allows the inventors to further optimize the rational design of the AMPs and membrane-selective peptides.

In accordance with an embodiment, the present invention provides a method for designing antimicrobial peptides comprising pore-forming, membrane-active peptides, comprising the steps of: a) providing a first template pore-forming, membrane-active peptide peptide; b) comparing the amino acid sequence of the first template peptide to the amino acid sequences of known pore-forming, membrane-active peptides located in a first antimicrobial peptide database; c) identifying similarities in hydrophobicity and amino acid sequence motif between the first template peptide and the known pore-forming, membrane-active peptides; d) identifying amino acid locations in the first template peptide which can be modified using the information from c); e) generating a plurality of modified pore-forming, membrane-active peptide sequences using the information from d); f) performing MD simulations on the plurality of modified pore-forming, membrane-active peptide sequences and determining whether the plurality of modified pore-forming, membrane-active peptide sequences have the physical characteristics of self-assembly into a pore-forming structure; g) synthesizing the plurality of modified pore-forming, membrane-active peptide sequences of e); h) testing the plurality of modified pore-forming, membrane-active peptide in an in vitro cell membrane testing system to determine efficacy of pore formation in cell membranes; and i) identifying one or more modified antimicrobial peptides when the membrane testing system gives a positive result.

In some embodiments, the above method is then used to create a library of positive modified antimicrobial peptides, which then are further analyzed with database guided high-throughput screening.

In accordance with another embodiment, the present invention provides a novel pore-forming, membrane-active peptide termed "LDKA" having the amino acid sequence GLLDLLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides.

In accordance with a further embodiment, the present invention provides a method of treating a microbial infection in a subject in need thereof comprising administering to the subject an effective amount of one or more antimicrobial peptides selected from the group consisting of GLLDLLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides.

It will be understood by those of skill in the art that one or more of the AMPs described herein can be combined in treatment of a subject.

In accordance with a still another embodiment, the present invention provides a method of treating a microbial infection in a subject in need thereof comprising administering to the subject an effective amount of a pharmaceutical composition comprising one or more antimicrobial peptides selected from the group consisting of GLLDLLKLLL-KAAG-COOH (LDKA; SEQ ID NO: 3, Table 1), GLLD-LLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAKLAGW-AMIDE (7D12; SEQ ID NO: 9, Table 1), GLLDLPKA-LAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) and a functional homolog of or functional fragment thereof; and a fusion polypeptide comprising an amino acid sequence of any of the above peptides, and a pharmaceutically acceptable carrier.

It is contemplated that the pore-forming, membrane-active peptides can be combined with other antibacterial or antimicrobial or antifungal agents. In a further embodiment, the medicament further comprises a second therapeutic agent. In some embodiments, the therapeutic agent is an anti-infective agent, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives.

As used herein, the term "infectious organisms" is synonymous with microbiological organisms that can infect the host subject. Prokaryotic organisms, such as bacteria, both gram-positive and gram-negative bacteria are included. One of ordinary skill would understand that in the context of the methods of the present invention, the definition also is inclusive of other microbiological organisms, which can infect a mammalian host. As such, organisms such as fungi, protozoa, parasites and also mammalian cells, which have been infected by certain viruses. Also, contemplated herein is AMPs that could be targeted to cancer cells.

In accordance with a further embodiment, the present invention provides a method of treating a microbial infection in a subject in need thereof comprising administering to the subject an effective amount of a pharmaceutical composition comprising one or more pore-forming, membrane-active peptides selected from the group consisting of GLLD-LLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAK-LAGW-AMIDE (7D12; SEQ ID NO: 9, Table 1), GLLD-LPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) or a functional homolog of or functional fragment thereof; or a fusion polypeptide comprising an amino acid sequence of any of the above peptides, at least one additional biologically active agent, and a pharmaceutically acceptable carrier.

In accordance with an embodiment, the present invention provides a method of treating a surface to prevent or remove microbial growth comprising applying to the surface an effective amount of one or more pore-forming, membrane-active peptides selected from the group consisting of GLLD-LLKLLLKAAG-COOH (LDKA; SEQ ID NO: 3, Table 1), GLLDLLHLLLKAAGW-AMIDE (K7H; SEQ ID NO: 4, Table 1), GLADLAKLLLKLLGW-AMIDE (7F3; SEQ ID NO: 5, Table 1), GLLDLLKLLLKLAGW-AMIDE (28H6; SEQ ID NO: 6, Table 1), GLDDLAKLLLKLAGW-AMIDE (25B2; SEQ ID NO: 7, Table 1), GLDDLLKALLKAAGW-AMIDE (4H9; SEQ ID NO: 8, Table 1), GLLDDAKLLAK-LAGW-AMIDE (7D12; SEQ ID NO: 9, Table 1), GLLD-LPKALAKALGW-AMIDE (7G6; SEQ ID NO: 10, Table 1), GLADAAKLLLKAAGW-AMIDE (11D12; SEQ ID NO: 11, Table 1), and GLLDAAKLLAKAAGW-AMIDE (24F1; SEQ ID NO: 12, Table 1) or a functional homolog of or functional fragment thereof; or a fusion polypeptide comprising an amino acid sequence of any of the above peptides.

In some embodiments, the method for treating a surface further comprises at least one additional antimicrobial or disinfecting agent. Disinfecting agents are known in the art and include compositions such as oxidizers, ammonia, ethanol, propanol, and other agents.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and unnatural amino acids. Many types of amino acid residues are useful in the adipokine polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

The term, "peptide," as used herein, includes a sequence of from four to 100 amino acid residues in length, preferably about 10 to 80 residues in length, more preferably, 15 to 65 residues in length, and in which the α-carboxyl group of one amino acid is joined by an amide bond to the main chain (α- or β-) amino group of the adjacent amino acid. The peptides provided herein for use in the described and claimed methods and compositions can also be cyclic.

Reference herein to "derivatives" includes parts, fragments and portions of the inventive LDKA peptides. A derivative also includes a single or multiple amino acid substitution, deletion and/or addition. Homologues include functionally, structurally or stereochemically similar peptides. All such homologues are contemplated by the present invention.

Analogs and mimetics include molecules, which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A partial list of known non-natural amino acid contemplated herein is shown in Table 2.

TABLE 2

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |

TABLE 2-continued

Non-natural Amino Acids

| Non-conventional amino acid | Code | Non-conventional amino acid | Code |
|---|---|---|---|
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Analogs of the subject pore-forming, membrane-active peptides contemplated herein include modifications to side chains, incorporation of non-natural amino acids and/or their derivatives during peptide synthesis and the use of cross-linkers and other methods which impose conformational constraints on the peptide molecule or their analogs.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilise 3D conformations, using homo-bifunctional crosslinkers such as the bifunctional imido esters having (CH$_2$)$_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of C$_\alpha$ and N$_\alpha$-methylamino acids, introduction of double bonds between C$_\alpha$ and C$_\beta$ atoms of amino acids and the formation of cyclic peptides or analogues by introducing covalent bonds such as forming an amide bond between the N and C termini, between two side chains or between a side chain and the N or C terminus.

In accordance with some embodiments, the pore-forming, membrane-active peptides of the present invention can be linked to an imaging agent for use in localizing infections in an organism or on a surface, or to show the activity of the agent.

The term "imaging agent," is known in the art. As used herein, the one or more imaging agents can be any small molecule or radionuclide, which is capable of being detected. In accordance with some embodiments the imaging agent is a fluorescent dye. The dyes may be emitters in the visible or near-infrared (NIR) spectrum. Known dyes useful in the present invention include carbocyanine, indocarbocyanine, oxacarbocyanine, thuicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes, which are active in the NIR region, are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with significantly improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

Routes of administration of the inventive pore-forming, membrane-active peptides include, but are not limited to intravenously, intraperitioneal, subcutaneously, intracranial, intradermal, intramuscular, intraocular, intrathecal, intracerebrally, intranasally, infusion, orally, rectally, via iv drip, patch and implant.

In one or more embodiments, the present invention provides pharmaceutical compositions comprising one or more of the inventive pore-forming, membrane-active peptides and a pharmaceutically acceptable carrier. In other aspects, the pharmaceutical compositions also include one or more additional biologically active agents.

With respect to the pore-forming, membrane-active peptides described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers, which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular AMP composition, as well as by the particular method used to administer the composition. Accordingly, there are a variety of suitable formulations of the pharmaceutical AMP composition of the invention. The following formulations for parenteral, subcutaneous, intravenous, intramuscular, intraarterial, intrathecal and interperitoneal administration are exemplary, and are in no way limiting. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the pore-forming, membrane-active peptides of the present invention that is administered should be sufficient to effectively target the microbe, or population of microbes in vivo, such that the stimulation of the neuronal cells can be detected, in the subject over a reasonable time frame. The dose will be determined by the efficacy of the particular AMP formulation and the location of the target population of microbes in the subject, as well as the body weight of the subject to be treated.

The dose of the AMP s of the present invention also will be determined by the existence, nature and extent of any adverse side effects that might accompany the administration of a particular AMP. Typically, an attending physician will decide the dosage of the AMP s with which to treat each individual subject, taking into consideration a variety of factors, such as age, body weight, general health, diet, sex, compound to be administered, route of administration, and the severity of the condition being treated. By way of example, and not intending to limit the invention, the dose of the AMP s of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the AMPs of the present invention can be at a concentration from about 1 nM to about 10,000 nM, preferably from about 10 nM to about 5,000 nM, more preferably from about 100 nM to about 500 nM.

As used herein, the terms "treat," "treating," "treatment," and the like refer to their use in reducing or ameliorating a disorder and/or symptoms associated therewith, for example bacterial or microbial infection. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition, for example, bacterial or microbial infection.

As used herein the term "therapeutically active agent" or "biologically active agent" means an agent useful for the treatment or modulation of a disease or condition in a subject suffering therefrom. Examples of therapeutically active agents can include any drugs, peptides, siRNAs, and conjugates, known in the art for treatment of disease indications.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

Further examples of biologically active agents include, without limitation, enzymes, antibiotics, antimicrobial agents, sterilizing agents and antibodies.

As used herein, the term "subject" refers to any animal. In some embodiments, the animal is a mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

Materials and Methods.

Peptide library synthesis. Peptide library was synthesized on Tentagel® $NH_2$ macrobeads with 280-320 μm particle size (~65,550 beads/g) using Fmoc solid-phase peptide synthesis. Each bead only has one peptide sequence. A photolinker is attached between peptide and bead. The quality of the peptide library was verified by mass spectrometry (e.g. MALDI) and Edman sequencing, and showed their sequences are correct. After placing one bead in each well of 96-well microplate, the photolinker between peptide and bead was cleaved with 5 hr of low-power UV light on dry bead, which were spreading to a dispersed single layer in a glass dish. The peptides were each dissolved in DMSO, quantified by tryptophan absorbance using Thermo Scientific™ NanoDrop microvolume spectrophotometers, and stored under −20° C. freezer.

Chemicals. LDKA peptides were synthesized and purified by GenScript Inc. with 98% purity. Peptide purity and identity were confirmed by HPLC and ESI mass spectrometry. The Nterminus and C-terminus were free amine group and free carboxyl group. 1-palmitoyl-2-oleoyl-sn-glycero-3-phosphocholine (POPC), 1-palmitoyl-2-oleoyl-sn-glycero-3-phospho-(1'-rac-glycerol) (POPG), and Hexadecanoyl Sphingomyelin (Egg SM) were purchased as dissolved in chloroform from Avanti Polar Lipids. All other solvents and reagents were all purchased from Fisher Scientific.

Large Unilamellar Vesicle (LUV) Preparation.

Lipids were dissolved in chloroform, mixed, and dried under nitrogen gas in a glass vial. Any remaining chloroform was removed under vacuum overnight. To make LUVs, lipids were resuspended in 10 mM sodium phosphate buffer (pH=7) with 100 mM potassium chloride. LUVs were generated by extruding the lipid suspension 10 times through 0.1 μm nucleopore polycarbonate filters to give LUVs of 100 nm diameter.

ANTS/DPX Leakage Assay.

5 mM ANTS and 12.5 mM DPX were entrapped in 0.1 μm diameter extruded vesicles with lipids. Gel filtration chromatography of Sephadex G-100 (GE Healthcare Life Sciences Inc.) was used to remove external free ANTS/DPX from LUVs with entrapped contents. LUVs were diluted to 0.5 mM and used to measure the leakage activity by addition of aliquots of LDKA. Leakage was measured after 3 hr incubation. 10% Triton was used as the positive control to measure the maximum leakage of the vesicle. Fluorescence emission spectra were recorded using excitation wavelength (Ex: 350 nm) and emission wavelength (Em: 510 nm) for ANTS/DPX using Synergy H1 Hybrid Multi-Mode Reader.

Macromolecule Release Assay.

Several different size dextrans were prepared and labelled with both TAMRA and biotin. Conjugated dextran was entrapped in POPC LUVs as described above. External dextran was removed by incubation with immobilized streptavidin. Streptavidin labelled with an Alexa-488 fluorophore was added during the leakage experiment with the peptide as previous described.[5] The sample was then incubated for 3 hr before measuring Alexa-488 fluorescence. A control without added peptide served as the 0% leakage signal and addition of 0.05% vol. Triton X-100 was used to determine 100% leakage.

Circular Dichroism (CD) Spectroscopy.

LDKA solutions (50 μM) in 10 mM phosphate buffer (pH 7.0) were co-incubated with 800 μM hRBC/bacterial model LUVs in identical buffer. CD spectra were recorded using the synchrotron radiation circular dichroism beamline on ASTRID at Aarhus University. Spectra were recorded from 270 to 170 nm with a stepsize of Δλ=0.5 nm, a bandwidth of 0.5 nm, and a dwell time of 2 s. Each spectrum was averaged over 3 repeat scans. The averaged spectra were normalized to molar ellipticity per residue. The raw data were analyzed using DichroWeb (dichroweb.cryst.bbk.ac.uk).

Bacterial Minimum Inhibitory Concentration (MIC).

*Escherichia colt* strain ATCC 25922, *Staphylococcus aureus* strain ATCC 25923, and *Pseudomonas aeruginosa* strain ATCC PAO1 were used in this study. Overnight cultures were subcultured to log phase ($OD_{600}$=0.3-0.6) after which cell counts were determined by measuring the $OD_{600}$ ($OD_{600}$ 1.0=1.5×$10^8$ CFU/mL for *S. aureus*, 5×$10^8$ CFU/mL for E. colt, and 2.04×$10^8$ CFU/mL for *P. aeruginosa*). Bacteria in minimal media mere added to serially diluted peptides and incubated for 3 hr, followed by the addition of full growth media. After overnight incubation, the optical density of the wells was recorded on a plate reader to determine whether they were sterilized (OD<0.08) or were at stationary phase growth ($OD_{600}$>0.5). Intermediate values, which were rare, were considered positive for growth. Average minimum sterilizing concentrations were calculated from the lowest peptide concentration that sterilized the bacteria in each serial dilution. The samples were done in sextuplet.

Hemolysis Assay.

Fresh human red blood cells were obtained from Interstate Blood Bank, Inc., and thoroughly washed in PBS until the supernatant was clear. hRBC concentration was determined using a standard hemocytometer. In hemolysis assays serial dilutions of peptide were prepared, followed by the addition of $2 \times 10^8$ hRBC/mL. After incubation for 1 hr at 37° C. the cells were centrifuged and the released hemoglobin was measured by optical absorbance of the heme group (410 nm). Negative control was buffer only (0% lysis), and the positive control was 20 μM melittin and distilled water (100% lysis). The samples were done in triplicate.

Molecular Dynamics (MD) Simulations and Analysis.

Unbiased all-atom molecular dynamics simulations were performed and analyzed using GROMACS 5.0.4 and Hippo BETA simulation packages (www.biowerkzeug.com), and VMD molecular visualization program (www.ks.uiuc.edu/Research/vmd). The pdb structure of extended peptides ($GL_5KL_6G$ (SEQ ID NO: 1), LDKL, and LDKA) were generated using Hippo BETA (see Table 3, Table 4, and Table 5). These initial structures were relaxed in the NPT ensemble using atomic detail Monte Carlo (MC) simulations for 200 MC steps, and water was treated implicitly using a Generalized Born implicit solvent.

Summary of the simulations. All systems contain 100 mM potassium chloride. LDKA* at 50° C. is the system that continues running for another 8 μs after 7 μs of LDKA at 70° C. hRBC: human red blood cell. DMPC: 1,2-dimyristoyl-sn-glycero-3-phosphocholine. Chol: cholesterol. PSM: N-palmitoyl-D-erythro-sphingosylphosphorylcholine. DMPG: 1,2-dimyristoyl-sn-glycero-3-phospho-(1'-rac-glycerol).

TABLE 4

| System | P:L | T [° C.] | Helicity [%] | Major TM Oligomer | H-Bond of P-P [#/peptide] | $\Delta G_{S \rightarrow TM}$ [kcal/mol] | $\Delta G_{interface}$ [kcal/mol] | $\Delta G_{trans\_TM}$ [kcal/mol] |
|---|---|---|---|---|---|---|---|---|
| $GL_5KL_6G$ (SEQ ID NO: 1) | 66:256 | 70 | 86 ± 2 | Dimer (24 ± 10%) | 10 ± 0 | 0.1 ± 0.4 | −5.42 | 0.66 |
| LDKL | 16:256 | 70 | 90 ± 2 | Tetramer (7 ± 7%) | 12 ± 0 | 1.2 ± 1.7 | −2.08 | 4.50 |
| LDKA | 16:256 | 70 | 70 ± 3 | Hexamer (13 ± 12%) | 10 ± 0 | 0.6 ± 0.6 | −0.62 | 5.21 |
| LDKA* | 16:256 | 50 | 78 ± 2 | Hexamer (14 ± 12%) | 11 ± 0 | 0.5 ± 0.2 | −0.62 | 5.21 |

Summary of peptide-assembling in the bacterial membrane (DMPC:DMPG=3:1) simulations. All systems contain 100 mM potassium chloride. $\Delta G_{Interface}$ and $\Delta G_{trans\_TM}$ represent the free energy of the peptide from water to POPC interface and the free energy of a helix from water to transmembrane inserted into POPC bilayer, respectively, and were estimated using Wimley-White Scale in MPEx software. LDKA* at 50° C. is the system that continues running for another 8 μs after 7 μs of LDKA at 70° C. POPC: 1-palmitoyl-2-oleoyl-sn-glycero-3-phosphocholine. hRBC: human red blood cell. DMPC: 1,2-dimyristoyl-sn-glycero-3-phosphocholine. Chol: cholesterol. PSM: N-palmitoyl-D-erythro-sphingosylphosphorylcholine. DMPG: 1,2-dimyristoyl-sn-glycero-3-phospho-(1'-rac-glycerol).

After relaxation, the peptides were placed in all atom peptide/lipid/water systems containing model membranes with 100 mM K and Cl ions using CHARMM-GUI (www.charmm-gui.org). Protein folding simulations were equilibrated for 10 ns with applying position restraints to the peptide. For pore-forming simulations, single peptides were allowed to folding onto the bilayer for ~600 ns; subsequently, the systems were multiplied by 4 times in both the x and y directions. Molecular dynamics simulations were performed with GROMACS 5.0.4 using the CHARMM36 force field, in conjunction with the TIP3P water model. Electrostatic interactions were computed using PME, and a cutoff of 10 Å was used for van der Waals interactions. Bonds involving hydrogen atoms were constrained using LINCS. The integration time-step was 2 fs and neighbor lists were updated every 5 steps. All simulations were performed in the NPT ensemble, without any restraints or biasing potentials. Water and the protein were each coupled separately to a heat bath with a time constant τT=0.5 ps using velocity rescale temperature coupling. The atmospheric pressure of 1 bar was maintained using weak semi-isotropic pressure coupling with compressibility $\kappa_z = \kappa_{xy} = 4.6 \; 10^{-5}$ bar$^{-1}$ and time constant τP=1 ps.

TABLE 3

| Peptide | Model Membrane | System† [Peptide/Lipid/Water] | Length [μs] | T [° C.] | Forcefield |
|---|---|---|---|---|---|
| $GL_5KL_6G$ (SEQ ID NO: 1) | Bacteria | 16/192 DMPC & 64 DMPG/10336 | 5 | 70 | CHARMM36 |
| LDKL | Bacteria | 1/48 DMPC & 16 DMPG/3641 | 5 | 70 | CHARMM36 |
| LDKL | Bacteria | 16/192 DMPC & 64 DMPG/9552 | 5 | 70 | CHARMM36 |
| LDKA | None | 1/None/810 | 3 | 70 | CHARMM36 |
| LDKA | hRBC | 1/20 DMPC & 20 Chol & 20 PSM/2757 | 5 | 70 | CHARMM36 |
| LDKA | Bacteria | 1/48 DMPC & 16 DMPG/3641 | 5 | 70 | CHARMM36 |
| LDKA | Bacteria | 16/192 DMPC & 64 DMPG/10208 | 7 | 70 | CHARMM36 |
| LDKA* | Bacteria | 16/192 DMPC & 64 DMPG/10208 | 8 | 50 | CHARMM36 |

TABLE 5

| Peptide | Membrane Model | T [° C.] | P:L | Helicity [%] | H-Bond of P-P [#/peptode] | Peptide Tilt Angle [°] |
|---|---|---|---|---|---|---|
| LDKL | Bacteria | 70 | 1:64 | 80.0 ± 7.7 | 8 ± 2 | 95.3 ± 15.2 |
| LDKA | None | 70 | — | 67.6 ± 8.0 | 8 ± 1 | — |
| LDKA | hRBC | 70 | 1:60 | 63.7 ± 2.1 | 8 ± 1 | 96.9 ± 12.7 |
| LDKA | Bacteria | 70 | 1:64 | 62.7 ± 3.7 | 8 ± 1 | 101.8 ± 12.0 |

Summary of protein folding simulations. All systems contain 100 mM potassium chloride. hRBC: human red blood cell.

Hydrophobicity Scale Analysis.

Hydrophobicity scale per residue of each N- and C-terminus are calculated by the antimicorbial peptides that have 12 or more amino acids in the APD. The partition free energy, which linearly corresponds to the hydrophobicity scale, was determined using Wimley-White hydrophobicity octanol-water scale[19] at the first six amino acids in the sequence for N-terminus and the last six amino acids for C-terminus. The average of the first and last six amino acids determine the hydrophobic scale in partition free energy per residue of the N- and C-terminus, respectively.

Statistical Sequence Analysis & Phylogenetic Tree.

We used the multiple sequence alignment score of the Clustal W algorithm, which is a commonly used progressive multiple sequence alignment method for protein sequences. It can evaluate the similarity between the amino acid sequences. The computer software is available on the website of the Kyoto University Bioinformatics Center, Kyoto, Japan (genome.jp/tools-bin/clustal). The pairwise alignment parameters for the analysis are K-tuple size=1, window size=5, gap penalty=3, and number of top diagonals=5. The multiple alignment parameters are gap open penalty=10, gap entension penalty=0.05, weight transition="NO", hydrophilic residues for proteins="GPSNDQERK" (SEQ ID NO: 26), hydrophilic gaps="YES", and select weight matrix="BLOSUM (for PROTEIN".

We compared LDKA peptide (sequence: GLLDLLKLLL-KAAG) (SEQ ID NO: 3) with LDKA as positive control (completely the same) and lb-AMP2 (sequence QYGRRCCNWGPGRRYCKRWC) (SEQ ID NO: 13) as negative control (completely different). Positive control (identical) has the alignment score of 69 and the alignment score of negative control (unlike) is −43. We defined the sequences are similar when alignment score equals or is above 15. The antimicrobial peptides that are similar to LDKA and have alignment score equals or is above 15 are further analyzed and filtered by their source, frog. Then, we applied phylogenetic tree to analyze these different species of frogs and their geographic location.

Example 1

Simulation-guided de novo design of AMPs from a simple peptide template.

The inventors showed that polyleucine-based peptides (e.g. acetyl-GL$_n$RL$_n$G-amide; n=5-8) (SEQ ID NO: 27) that have the basic characteristic required of an AMP: they bind strongly to lipid bilayers[20] and continuously flip between surface bound (S) and transmembrane (TM) inserted helical conformations.[21] To design an AMP starting template, the inventors first modified this sequence to GL$_5$KL$_6$G (NH$_3^+$-GLLLLLKLLLLLLG-CO$_2^-$) (SEQ ID NO: 1, Table 1) replacing arginine with lysine since glycine, leucine, and lysine are the most abundant amino acids in short helical AMP sequences.[18] The neutral acetyl and amide termini are replaced by charged amino (NH$_3^+$—) and carboxy (—CO$_2^-$) terminal groups to increase solubility and promote pore-forming electrostatic peptide-peptide interactions.[22] The hydrophobic length is selected to lie between GL$_5$RL$_5$G (SEQ ID NO: 28), which is 7±2% transmembrane (TM) inserted and GL$_6$RL$_6$G (SEQ ID NO: 29), which is 35±8% TM inserted, aiming for a predominantly surface bound peptide consistent with typical AMPs.

Unbiased equilibrium simulations show that this peptide spontaneously inserts into bacterial model membranes (DMPC:DMPG=3:1). In these simulations, a single fully extended peptide is initially placed in bulk solution and allowed to fold and partition freely into and out of the lipid bilayer.[20] After ~500 ns equilibration, during which the peptide absorbs and folds onto the membrane interface, the system is replicated 16× in the membrane plane, forming a 4×4 matrix, which serves as the starting configuration for a spontaneous oligomerization simulation.[17] All simulations are run at 70° C. to increase pore-formation kinetics. We have previously demonstrated that elevating the temperature does not change conformational equilibria or partitioning energies of helical membrane-active peptides, provided they are stable against thermal denaturation; however, the vast increase in sampling kinetics at high temperatures allows simulation of peptide folding, bilayer partitioning, and oligomerization without the need for advanced sampling techniques that may bias the system.[17,20,21,23,24]

Figure 1A:
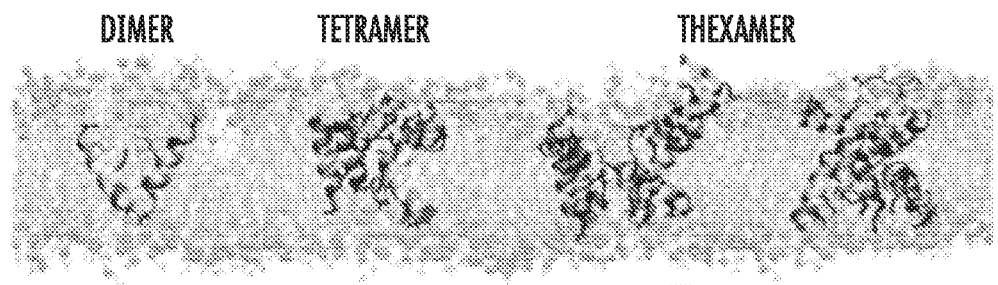
FIGS. 1A-1D show that unbiased multi-microsecond MD simulations reveal the spontaneous assembly of designed sequences into oligomeric structural ensembles in the membrane. All peptides are initially placed on the surface (S) of one membrane leaflet. 1A. Snapshots of the dominant structure from each simulation (side and top view). The positively charged N-terminus and cationic lysine residues are colored blue, while the negatively charged C-terminus and anionic aspartic acids are shown in red. Surface bound peptides that are part of the oligomeric TM assembly are shown in green. 1B. TM oligomer analysis of (1B) $GL_5KL_6G$ (SEQ ID NO: 1), (1C) LDKL, and (1D) LDKA in the bacterial membrane model. The predominant multimers in these systems are dimers (for $GL_5KL_6G$ (SEQ ID NO: 1), trimers (for LDKL), and hexamers (for LDKA), respectively. Octamers were the largest channels observed. Aggregates of more than 8 peptides exist, but consist of several lower order assemblies in lateral contact, and occur infrequently.
Figure 1B:
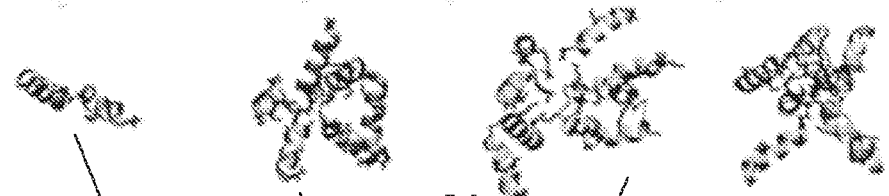
Figure 1B:
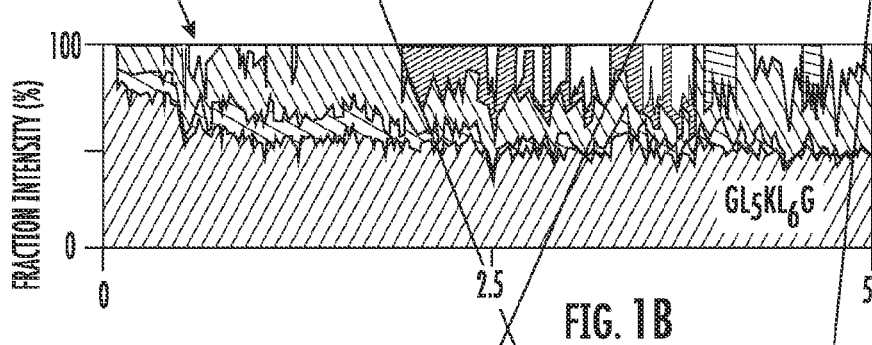
Figure 1B:
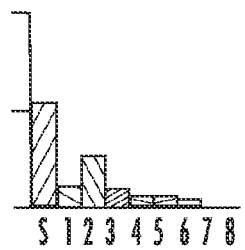
Figure 5:
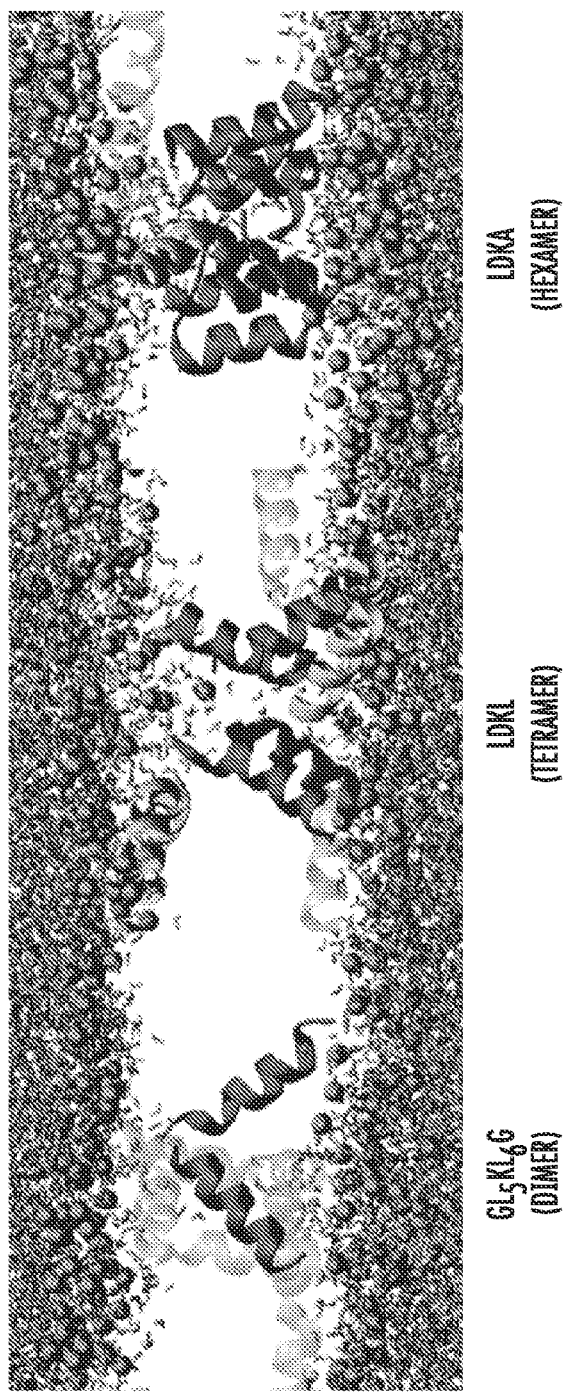
FIG. 5 Snapshot of the water conducting of each dominant structure in the $GL_5KL_6G$ (SEQ ID NO: 1) (dimer), LDKL (tetramer), and LDKA (hexamer) simulations. Red peptides are the TM peptides that are counted in the oligomer. Green peptides are located on the membrane surface but form part of the oligomeric membrane-spanning channel structure. Grey peptides are part of the simulation system, but do not form part of the channels.

The peptides were initially placed on the same side of the membrane. FIGS. 1A-1D show that GL$_5$KL$_6$G (SEQ ID NO: 1) peptides spontaneously insert into lipid bilayers forming the antiparallel TM dimer. TM insertion occurs mostly from peptide-peptide interactions between two membrane surface-bound (S) peptides and few of them TM inserts using hydrophobic effect. The associated free energy change of $\Delta G_{S \to TM}$ is 0.1±0.4 kcal/mol. For equilibrium simulations, where peptides alternate continuously between S and TM configurations, this can be determined directly using $\Delta G_{S \to TM}$=−RT ln($p_{TM}$/ps), where R is the ideal gas constant and T is the temperature, and $p_{TM}$ and $p_S$ are the normalised populations of the TM and S states, respectively. Membrane inserted configurations are dominated by V-shaped anti-parallel TM dimers (FIGS. 1A-1D & Table 4), which are stabilized by hydrogen bonding between the charged terminal amino (—NH$_3^+$) and carboxyl (—CO$_2^-$) groups (FIG. 1A & FIG. 1B). However, no pore formation is observed within the 5 μs timeframe of the simulation (FIG. 5).

Figure 1C:
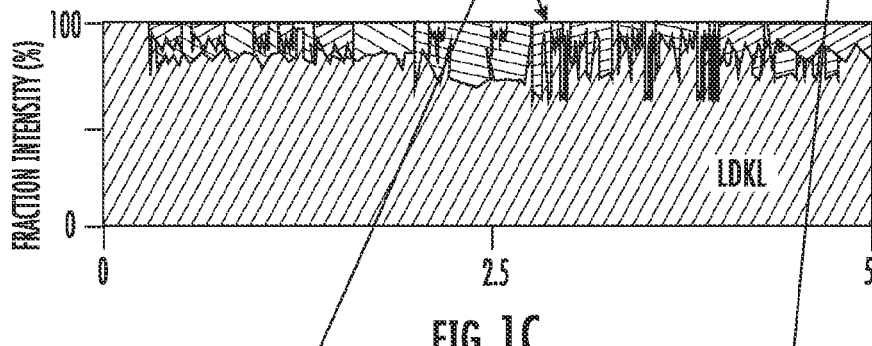
Figure 1C:
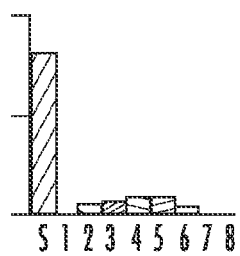

This dimer structure was then used to guide mutations to induce channel formation. First, two mutations: L4D and L11K, were introduced that turn two leucine residues located on the same helical face as the central Lys7 into charged amino acids, while keeping the overall charge of the peptide constant at +1. The rationale behind these mutations is to encourage the formation of higher-order oligomeric structures in the membrane by introducing more potential electrostatic interactions between neighbouring peptides. Oligomerization simulations of this new peptide, NH$_3^+$-GLLDLLKLLLKLLG-CO$_2^-$ (LDKL) (SEQ ID NO: 2), indeed reveal the formation of a water-conducting tetramer within 2 μs (FIG. 1C, FIG. 5, & Table 4). This structure is stabilized for the remainder of the simulation by an average of 12 inter- and intra-peptide hydrogen bonds per peptide, two more than for GL$_5$KL$_6$G (SEQ ID NO: 1). As expected, these two additional hydrogen bonds are formed by the carboxylate anion of Asp4 interacting with the protonated amino groups of Lys7 and Lys11. This structure is surrounded by a number of surface bound peptides that that are in contact with the channel-forming peptides (FIG. 1A). LDKL has an insertion free energy barrier of $\Delta G_{S \rightarrow TM}$=1.2±1.7 kcal/mol, which is higher than $GL_5KL_6G$ (SEQ ID NO: 1) ($\Delta G_{S \rightarrow TM}$=0.1±0.4 kcal/mol) due to its shorter hydrophobic length and two additional charged residues (Table 4). It results in making the surface bound predominants as desired for an AMP.

Figure 1D:
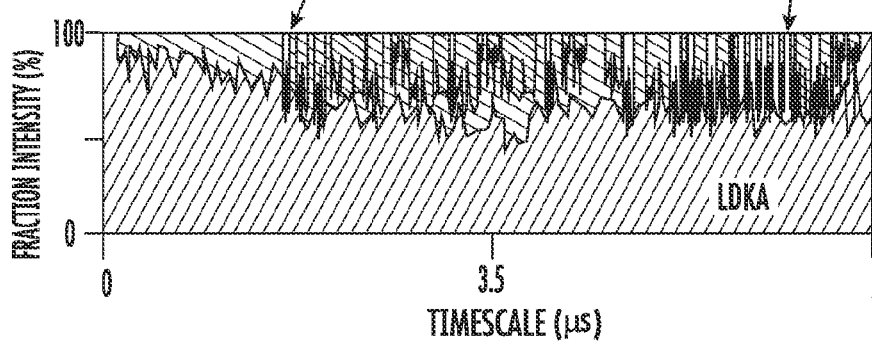
Figure 1D:
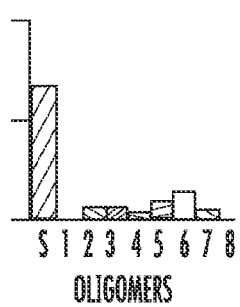
Figure 2A:
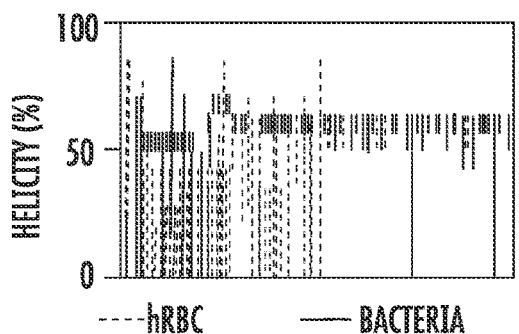
FIGS. 2A-2E show spontaneous folding of LDKA with hRBC and bacterial membrane models at 70° C. (2A) Corresponding evolution of the helicity. (2B) Insertion depth of Lys7 of LDKA in membrane lipids. (2C) The density cross-section profile of the bilayer shows that the folded surface-bound (S) state LDKA peptide is buried below the water interface, and has overlap with the phosphate headgroups (PC & PG) and carbonyl-glycerol (C/G) group. Snapshots of LDKA binding and folding with (2C) bacterial and (2D) human red blood cell (hRBC) model membranes. Ribbons colored blue to red from N- to C-terminus, and positive and negative charged sidechains are shown as blue and red, respectively. Orange sphere represents the phosphate headgroup of the zwitterionic lipids (PC), and yellow sphere shows the phosphate headgroup of the anionic lipids (PG).
Figure 2B:
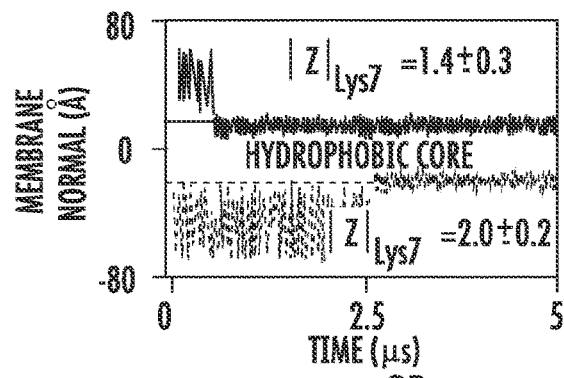
Figure 2C:
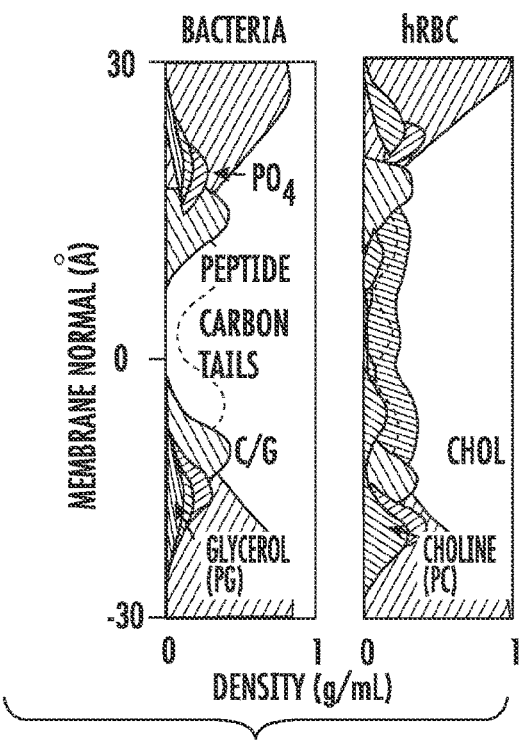
Figure 2D:
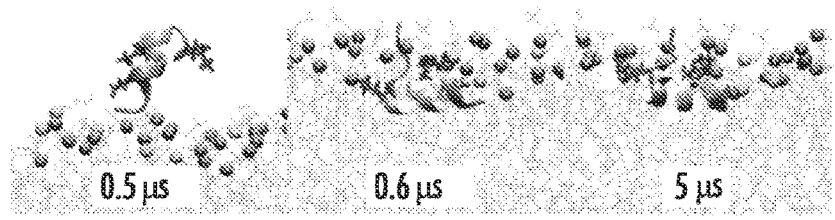
Figure 2E:
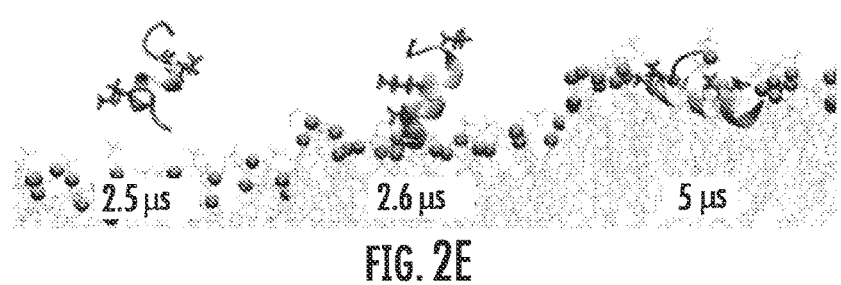
Figure 6:
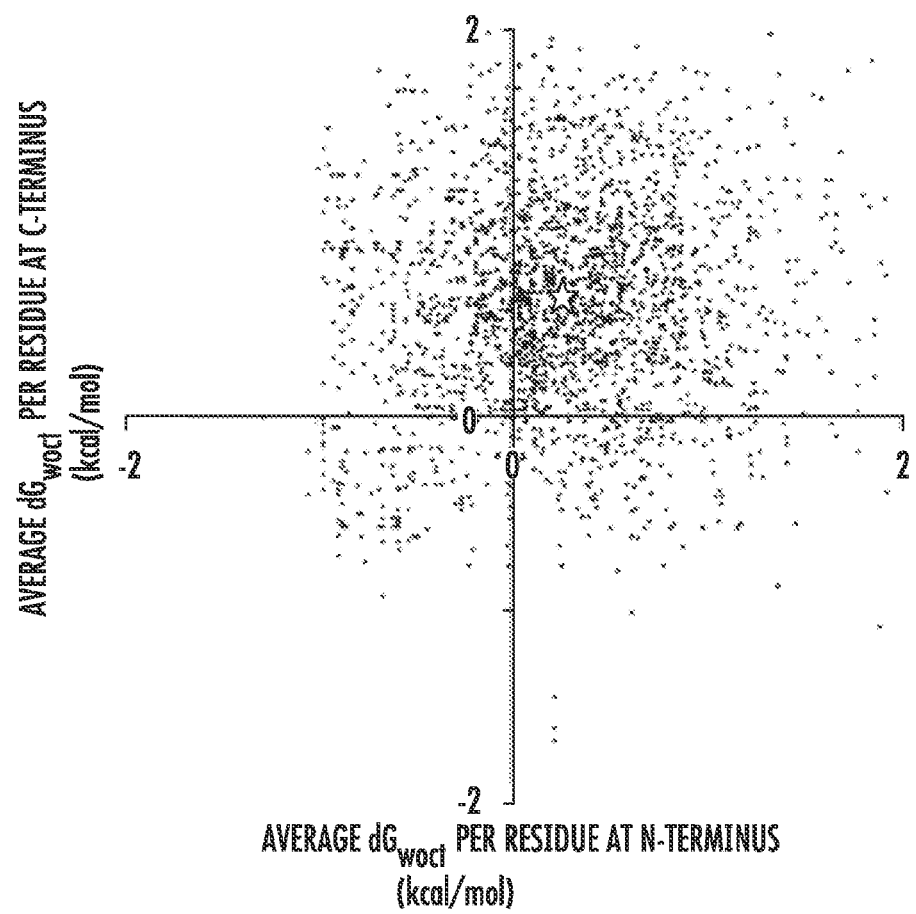
FIG. 6 Hydrophobicity scale per residue of the N- and C-terminus of 2,579 AMPs (with peptide length≥12 amino acids) in the Antimicrobial Peptide Database (APD).[4,18] The partition free energy was determined using Wimley-White scale[19] at the first six amino acids in the sequence for N-terminus and the last six amino acids for C-terminus. Red star and the free energy are the overall average of 2,579 AMPs. The average hydrophobicity scale per residue of the N-terminus ($\Delta G_{avg,N-term}$) is 0.3±0.6 kcal/mol and the average hydrophobicity scale per residue of the C-terminus ($\Delta G_{avg,c-term}$) is 0.6±0.6 kcal/mol.

In the next step, we compared our LDKA peptide with known AMP sequences to guide mutations that improve peptide solubility, channel formation efficiency, and pore size. Analysis of the Antimicrobial Peptide Database (APD) shows that on average ~60% of amino acids in AMP sequences are hydrophobic,[18] which is likely to directly influence peptide solubility. In APD, we found most of the AMPs have less hydrophobic in their C-termini with an average water-to-octanol per-residue partitioning free energy of $\Delta G_{woct,C-ter}$=0.6±0.6 kcal/mol for the C-termini, whereas the N-termini $\Delta G_{woct,N-ter}$=0.3±0.6 kcal/mol. FIG. 6 shows that although this difference $\Delta\Delta G_{woct}$ is small but statistically significant. Higher $\Delta G_{woct}$ means less hydrophobic, and lower $\Delta G_{woct}$ implies more hydrophobic. This value was calculated by averaging over 6 consecutive terminal residues of all AMPs in the APD that have 12 or more amino acids in the sequence using the Wimley & White hydrophobicity scale.[19] To incorporate this into our peptide, two leucines at the C-terminus of LDKL are substituted for two alanines (L12A and L13A), resulting in a new sequence: $NH_3^+$-GLLDLLKLLLKAAG-$CO_2^-$ (LDKA) (SEQ ID NO: 3). The C-terminal-AAG motif is common in AMPs (e.g. Hylaseptin P1: GILDAIKAIAKAAG, (SEQ ID NO: 14) which remarkably also shares similar charge and hydrophobic residue spacings) and lowers both the hydrophobicity and helical propensity of the C-terminus. Counter-intuitively, simulations show that the less hydrophobic LDKA peptides have a slightly increased TM insertion propensity (34±8%) compared to LDKL (22±8%), despite a decreased overall helicity from 90±2% (LDKL) to 70±3% (LDKA), which is reflected in an increased structural plasticity and experimental solubility (Table 4). This increase in the TM inserted peptide fraction is due to the formation of larger water-conducting oligomeric assemblies. FIGS. 1A-1D show that a water-conducting hexamer (FIG. 5), which forms within 2 μs, remains the dominant intra-membrane oligomeric assembly for this peptide (FIG. 1D & Table 4). Like LDKL, the channel-like structure formed by LDKA is surrounded by several surface bound peptides, which extends the hydrophobic length of the structure, resulting in a better hydrophobic match (FIGS. 1A-1D & FIG. 5).

Our previous work shows that the free energy of TM insertion in zwitterionic POPC bilayer of $GL_nRL_nG$ (SEQ ID NO: 27) is linearly related to the hydrophobic length of the peptide: $\Delta G_{S \rightarrow TM}$=m·$n_{Leu}$+b, where $n_{Leu}$ is the number of leucines in the sequence, while m is the increase in insertion free energy per leucine and b is a constant. LDKA, which consists of a total of 14 amino acids including 7 leucines, has a hydrophobic length that is lower than both $GL_5RL_5G$ (SEQ ID NO: 28) and $GL_6RL_6G$ (SEQ ID NO: 29). The latter peptides have $\Delta G_{S \rightarrow TM}$ values of 2.1±0.2 kcal/mol ($p_{TM}$=7%) and 0.5±0.3 kcal/mol ($p_{TM}$=35%), respectively.[21] Nevertheless, the computed $\Delta G_{S \rightarrow TM}$ of LDKA is 0.6±0.6 kcal/mol, which is similar to the much more hydrophobic $GL_6RL_6G$ (SEQ ID NO: 29) peptide. FIGS. 1 and 2 show that unlike the $GL_nRL_nG$ (SEQ ID NO: 27) family of peptides, which spontaneously TM-insert into the membrane as monomers, LDKA does not insert as a monomer. Instead, LDKA relies on peptide-peptide interactions to bury the extra charged residues in a water filled pore.[22] It shows the number of inter-helical H-bonds of a single folded LDKA peptide (total 1 peptide in the simulation to study its folding) is 8±1, which the amine group (N—H) of backbone donates a hydrogen bond to the backbone carbonyl group (C=O) of the amino acid located three or four residues before along the peptide sequence. Multiple LDKA peptides (total 16 peptides in the simulation to study its assembly) in pore-assembly simulations result in total 11±0 inter- and intra-helical H-bonds per peptide (Table 4 and Table 5). These three intra-helical H-bonds come from the P-P interactions of the carboxyl group (C(=O)OH) of charged C-terminus or Asp4 offers a hydrogen bond acceptor for the amino group of charged N-terminus, Lys7, or Lys11.

Example 2

Figure 7:
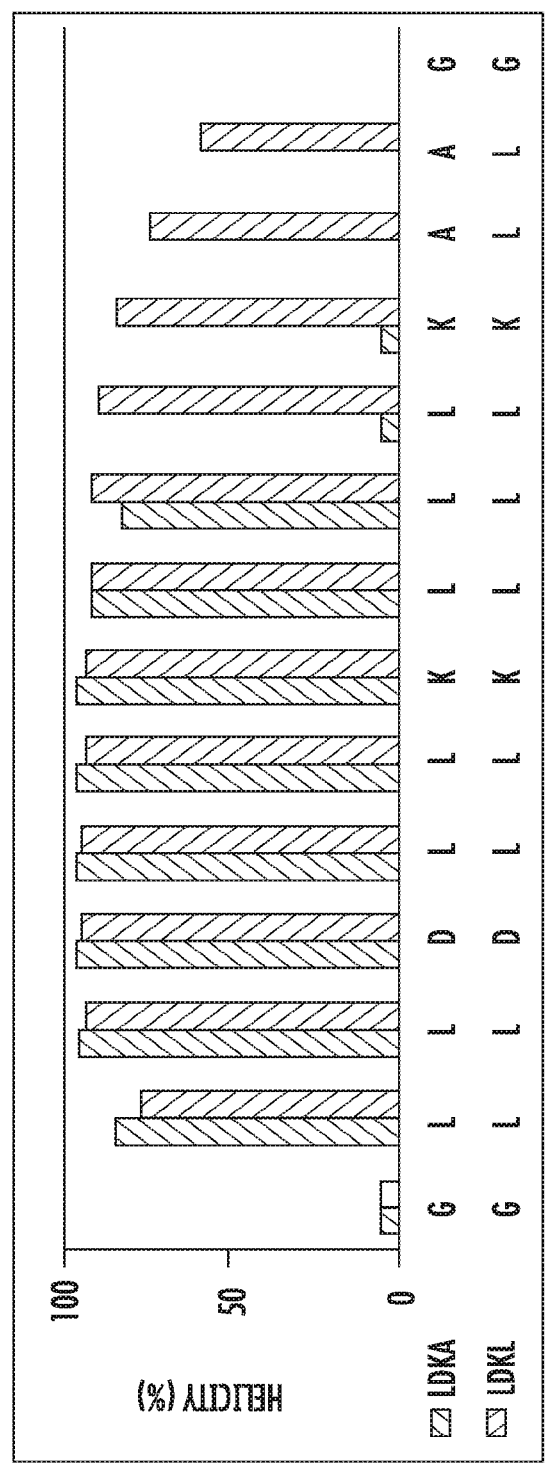
FIG. 7 Helicity of helical folding per amino acid of each LDKA (SEQ ID NO: 3, top row) and LDKL (SEQ ID NO: 2, bottow row) with bacterial model membranes, which corresponds to the peptide binding. Higher helical fraction corresponds stronger peptide binding to the membrane, and lower helical fraction is equivalent to weaker peptide binding to the membrane.

In addition to spontaneously assembling into functional pores, the biological activity of pore-forming AMPs depends crucially on their ability to bind strongly to lipid bilayers without precipitating out of aqueous solution. Unbiased peptide folding-partitioning simulations of a single peptide (FIGS. 2A-2E) predict that LDKA strongly binds and folds onto both human red blood cell (hRBC) (DMPC:PSM: CHOL=1:1:1) and bacterial (Bac) model membranes (DMPC:DMPG=3:1). The peptide, which is initially placed in a fully extended conformation in bulk aqueous solvent>15 A from the membrane spontaneously absorbs and folds onto the interface of the bilayers. No dissociation events are observed over the 5 μs simulation timescale, suggesting strong binding. Unlike many other membrane active peptides we have studied previously, LDKA acquires some helicity in solution before binding to the membrane interface. Once bound, the helicity of monomeric peptides remain ~63% for both hRBC and bacterial model membranes (Table 5), and the C-terminal-AAG motif remains mostly coiled (FIG. 7).

Figure 4A:
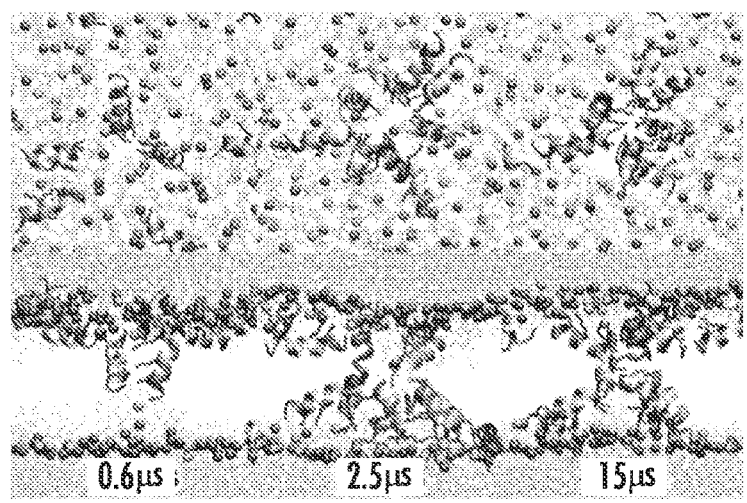
FIGS. 4A-4D LDKA hexamer structural stability simulation at 70° C. for 7 µs (0-7 µs) and continues at 50° C. for another 8 µs (7-15 µs). The green dash line indicates the time frame that has the temperature change from 70 to 50° C. (4A) Snapshots of top and side views of peptides assemble on the surface of the membrane, insert as dimer into the membrane, and form a pore in the membrane. Red sphere indicates the N-terminus (GLY-1). Positive and negative-charged residues are shown in blue and red, respectively. Orange sphere and yellow sphere represent the phosphate headgroup of DMPC and DMPG, respectively. (4B) Helical fraction and number peptide crossing the membrane of LDKA assembling. (4C) Normalized distribution in z-axis of LDKA in the membrane. Lys7 was used as a label to track all the LDKA peptides. (4D) TM multimer analysis shows that the tetramer is the dominant conformation over the 15 µs timescale of the simulation. The dashed green line shows where the simulation temperature was reduced from 70 to 50° C.
Figure 4B:
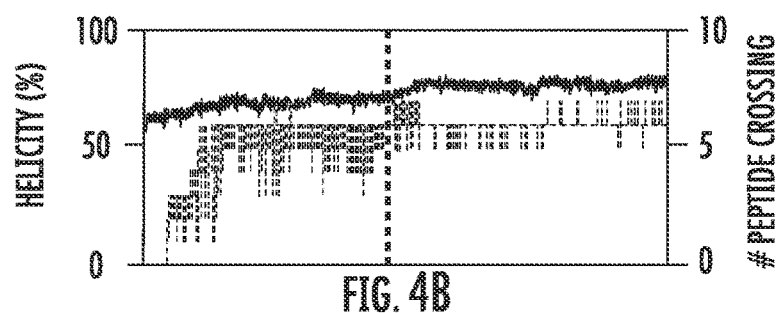
Figure 4C:
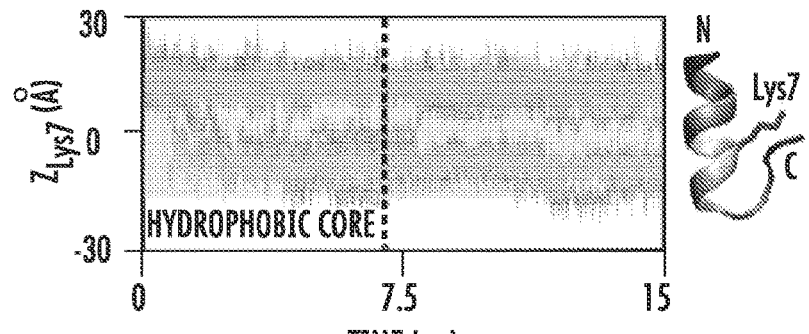
Figure 4D:
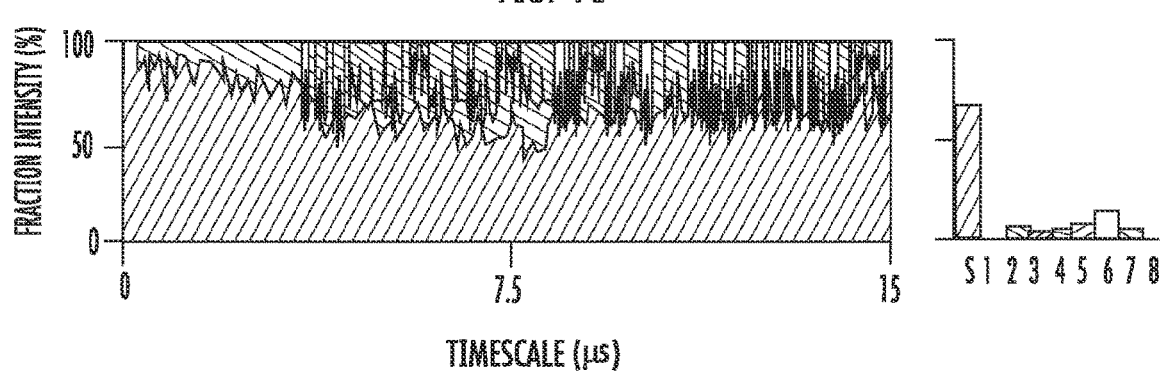
Figure 9:
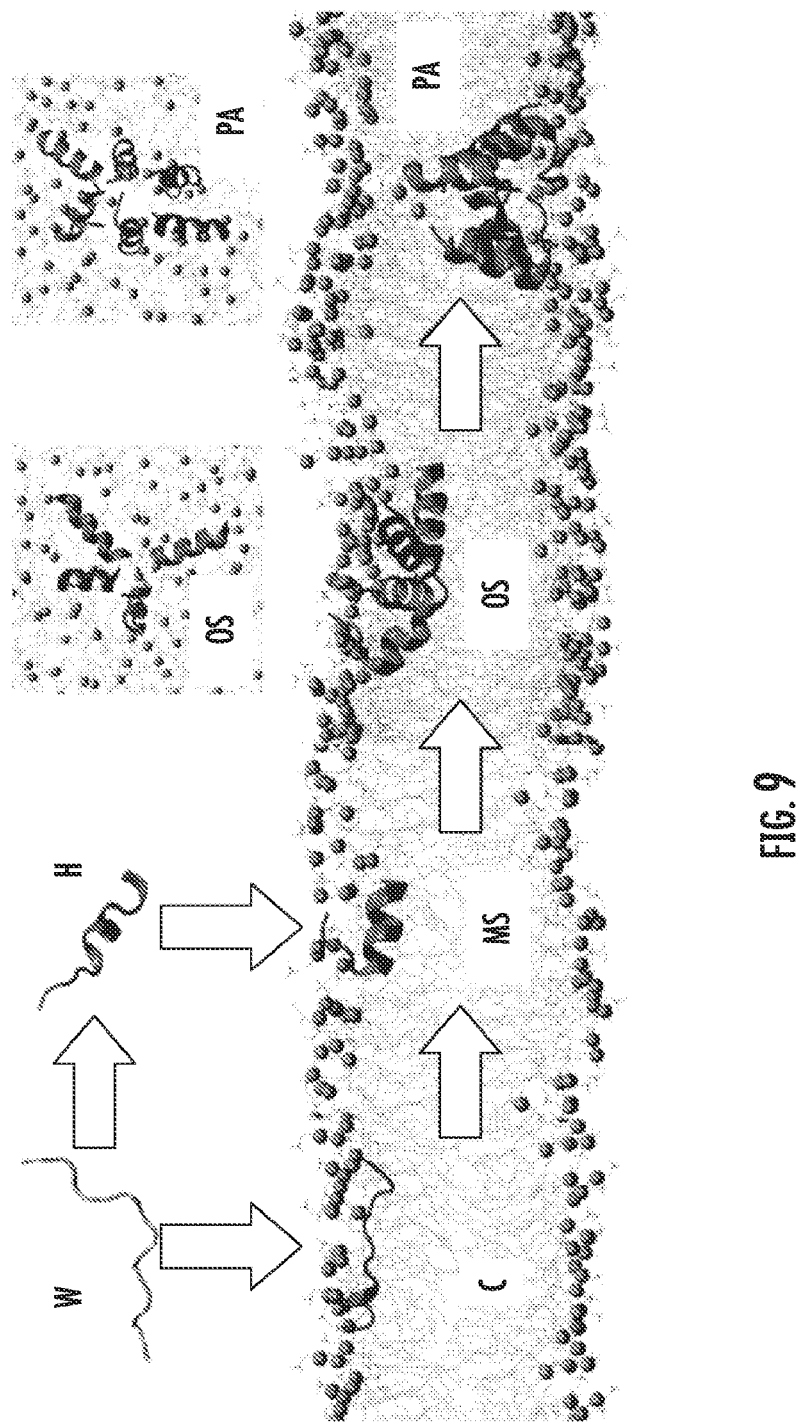
FIG. 9 Schematic partitioning for disordered toroidal pore peptides. Three states are populated at equilibrium: an α-helix bound on the membrane surface (MS), an oligomeric surface state (OS), and peptide-assembly (PA) in the membrane. We did not observe a water-soluble (W) state and coiled bound (C) state. Helix in water (H) state is a prior mechanism before peptide binding and folding onto the membrane in LDKA simulation.

To investigate the structural stability and plasticity of the LDKA pore-assembly we extended the simulation in the bacterial model membrane to 15 μs (FIGS. 4A-4D). For this, we took the last frame of the 70° C. LDKA assembly simulation at 7 μs and continued this simulation for another 8 μs at 50° C. This revealed three equilibrium states: an α-helix bound on the membrane surface (S), an oligomeric surface fold (OS), and peptide-assembly (PA) in the membrane (FIG. 9). We observed that surface bound peptides in both the upper and bottom leaflets further extend the hydrophobic length of the pore helping to stabilize the structure (FIG. 4A). FIGS. 4A-4D show that LDKA peptides flip between S and TM states and are able to cross the hydrophobic core of the bilayer, either via mutual burial of their hydrophilic groups or via shuttling them through the aqueous pore of the oligomeric assembly. Over the 15 μs timescale of the simulation the dominant structure is a dynamic and disordered hexamer (FIG. 4D).

Example 3

To validate the simulation-guided peptide design methodology LDKA was solid-phase synthesized, purified, and functionally characterized in vitro using biophysical techniques and biological assays.

FIG. 3A shows circular dichroism (CD) spectra of LDKA in aqueous solution as well as in the presence of modeled hRBC and bacterial model membrane large unilamellar vesicles (LUVs) at pH=7. The lipid composition of the vesicles was identical to the simulations and the results confirm that LDKA is indeed soluble (<0.1 mg/mL in 1×pH 7.4 DPBS) and partially helical in solution, and spontaneously binds to both membrane types, increasing the helicity from 45% to 78%. The helical fraction of membrane-bound LDKA peptides agrees with the equilibrium LDKA assembly simulations at 50° C., which is 78±2% (Table 4), while the aqueous helicity is lower in the experiment, suggesting a structural bias in the molecular simulation force field.

Pore-formation was determined using a membrane leakage assay. This assay measures the amount of liposome-encapsulated dye released into the supernatant by pores forming in the liposomal membrane or by membrane disruption after addition of LDKA. FIG. 3B shows that LDKA results in fluorescent dye leakage from both hRBC and bacterial model vesicles. Leakage is stronger for bacterial model vesicles with >50% release of ANTS/DPX (350 Da) dyes even at very low peptide-to-lipid (P/L) ratios of 1/1000. Variation of the molecular weight of the encapsulated dye (350 Da ANTS/DPX fluorophores and 10-kDa dextrans) allows estimating the size of the membrane pore. While leakage from bacterial vesicles is ~100% at P/L>1/50, irrespective of the dye size, leakage of the larger 10-kDa dextrans is only a fraction of the small dye leakage for P/L<1/100. This suggests that LDKA forms an ensemble of pores of different sizes, with smaller pores dominating at low P/L ratios. A similar ensemble of structurally different membrane pores has recently been demonstrated for the naturally occurring AMP maculatin.[17]

Biological activity of LDKA is determined using a bacterial minimum inhibitory concentration (MIC) assay and a hemolysis assay. The results are summarized in FIG. 3C, demonstrating that LDKA has antibacterial activity against both gram-positive (*S. aureus*) and gram-negative (*E. coli* and *P. aeruginosa*) bacteria in nutritionally rich medium, with MICs in the 10-70 μM range, which are typical for naturally occurring AMPs.[25-31] FIG. 3D shows that similar to human indolicidin[32], which is a short 13-residue natural AMP, LDKA causes minimal damage (less than 5% fractional hemolysis) to hRBCs below concentrations of 20 μM. Above this concentration hemolysis is ~3× that of indolicidin. This suggests that LDKA has sufficient antimicrobial potency and selectivity for a potential pharmaceutical application against *S. aureus* at 10 μM.

Example 4

Development of a database-guided high-throughput screen to identify peptides that have different pore sizes and membrane selectivities.

Figure 8A:
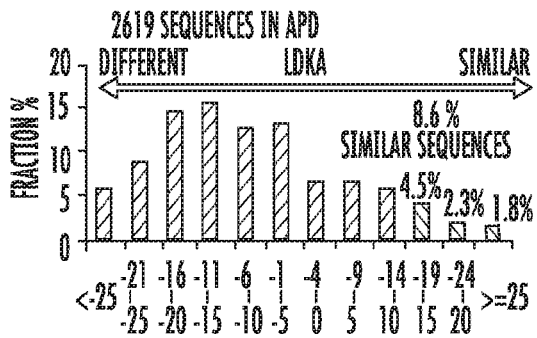
FIGS. 8A-8C Alignment score of LDKA with the antimicrobial peptides database presents sequence similarity of LDKA with the (8A) all the peptide sequences, and (8B) peptide sequences from frog. Alignment score 15 was used as a cutoff to distinguish the different and similar sequences. (8C) Phylogenetic tree of frogs that have LDKA-like antimicrobial peptides with alignment score≥15. The colored circles next to each species are their occurrence of continents (Red: Africa, orange: Asia, yellow: Australia, green: Europe, blue: North America, and purple: South America).
Figure 8B:
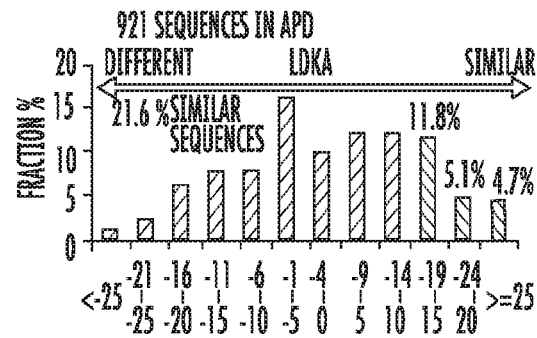
Figure 8C:
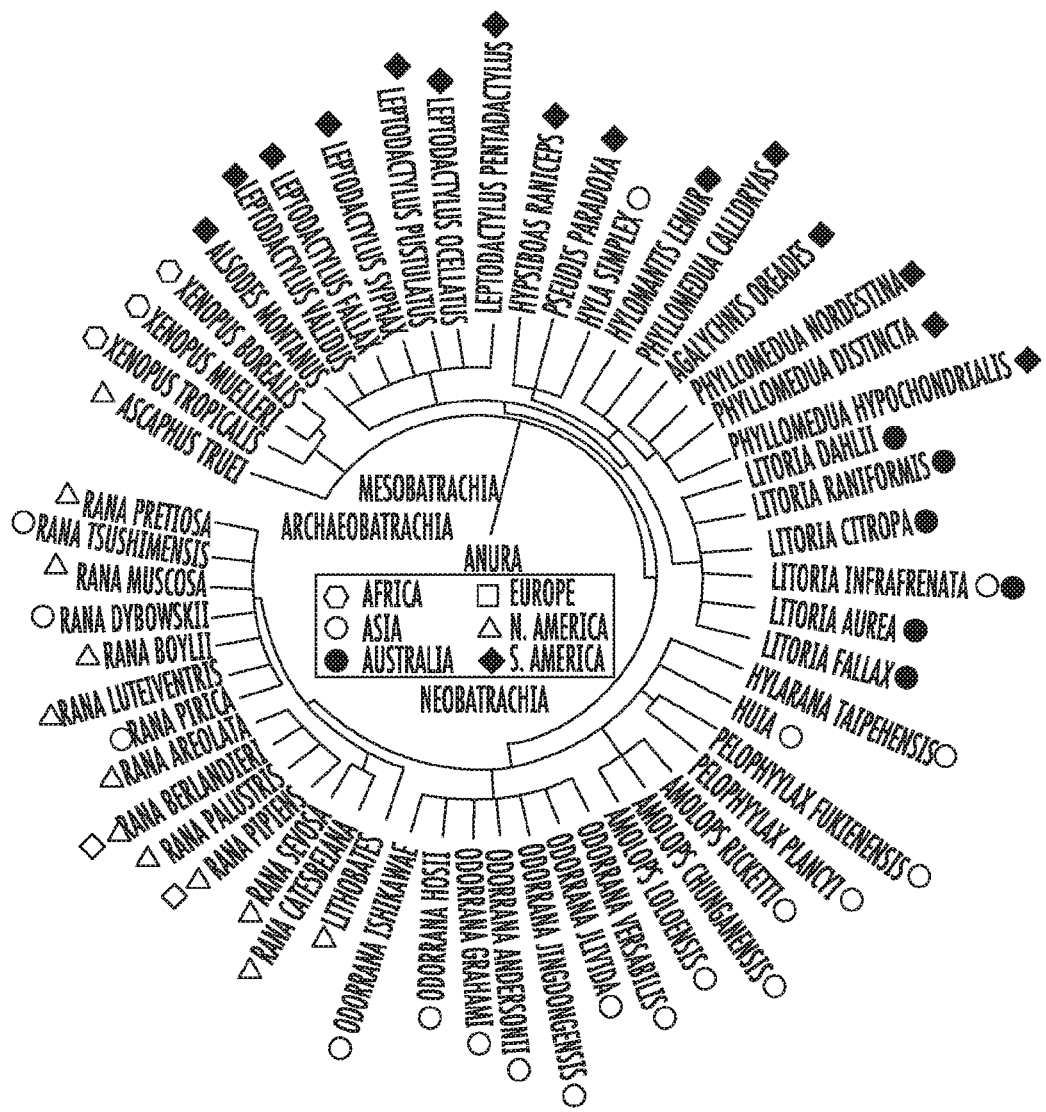

Analysis of known AMPs reveals that many sequences have N-terminal GhhD motifs, and contain KhhhK (amino acids 7 to 11 of SEQ ID NO. 30) motifs in the middle of their sequences,[4,18] where the 'h' denotes a hydrophobic residue. Remarkably, the simple LDKA peptide has both features. Further comparison of LDKA with the 2,619 sequences in the APD[4] revealed that 224 AMPs share a similar motif (GhhDhhKhhhKhhG (SEQ ID NO. 30)) with LDKA (FIG. 8A). More specifically, 199 of them are the AMPs from frogs, which show that 21.6% of the AMPs in frogs (sample size: 921 sequences from frogs in APD) contain a motif that is similar (alignment score≥15) to LDKA (FIG. 8B), and these frogs are distributed all over the world (FIG. 8C). It is possible that this common motif of LDKA in frogs is caused by both genomic evolution and it is the optimized sequence in this context, which reveals that this sequence motif is conserved since the break-up of the Pangea supercontinent in the middle of the Jurassic ~175 million years ago.[33] The alignment score of LDKA and the APD shows that LDKA shares similar sequences with many short AMPs (Table 6), e.g. Hylaseptin P1,[25] Hylain 2,[26] DFTamP1,[18] Frenatin 2,[27] Aurein 1.1,[28] Dahlein 1.1,[29] Fallaxidin 3.1,[30] and Uperin 7.1.[31] These peptides all have helical lengths of 20-24 Å (assuming an ideal α-helix with a length of 1.5 Å per residue), which is too short to span the ~27 Å hydrophobic membrane thickness of *E. coli*.[15,16] Our simulations suggest that these short AMPs rely on several interactions to cross the membrane barrier (FIG. 9), and our study of LDKA reveals how these peptides disrupt bacterial membranes by forming pores that involve surface bound peptides to compensate for the short length of the folded peptide, which is insufficient to span the bilayer on its own.

TABLE 6

| Peptide | Source | Sequence | Alignment Score | Net Charge at pH 7 | $\Delta G_{Interface}$ [kmol/cal] |
|---|---|---|---|---|---|
| LDKA | Ab initio design | GLLDLLKLLLKAAG (SEQ ID NO: 3) | 69 (Identical) | +1.0 | -0.62 |
| Ib-AMP2 | *Impatiens balsamina* | QYGRRCCNWGPGRRYCKRWC (SEQ ID NO: 13) | -43 (Unlike) | +5.7 | -0.29 |
| HSP1 | *Hyla punctata* South America | GILDAIKAIAKAAG (SEQ ID NO: 14) | 42 | +1.0 | 2.32 |
| Hylain 2 | *Hyla simplex* China | GILDPIKAFAKKAAG (SEQ ID NO: 15) | 39 | +1.0 | 1.78 |
| DFTamP1 | Ab initio designed | GLLSLLSLLGKL (SEQ ID NO: 16) | 36 | +1.0 | -3.48 |
| Frenatin 2 | *Litoria infrafrenata* Australia | GLLGTLGNLLNGLGL (SEQ ID NO: 17) | 31 | 0 | -3.16 |
| Aurein 1.1 | *Litoria aurea* & *Litoria raniformis* Australia | GLFDIIKKIAESI (SEQ ID NO: 18) | 28 | 0 | 2.34 |

TABLE 6-continued

| Peptide | Source | Sequence | Alignment Score | Net Charge at pH 7 | $\Delta G_{Interface}$ [kmol/cal] |
|---|---|---|---|---|---|
| Dahlein 1.1 | Litoria dahlii Australia | GLFDIIKNIVSTL (SEQ ID NO: 19) | 27 | 0 | -0.46 |
| Fallaxidin 3.1 | Litoria fallax Australia | GLLDLAKHVIGIASKL (SEQ ID NO: 20) | 26 | +1.1 | 1.60 |
| Uperin 7.1 | Litoria ewingi Australia | GWFDVVKHIASAV (SEQ ID NO: 21) | 23 | +0.1 | 0.31 |

Summary of the peptide sequences of LDKA, and their analogues. Alignment score was calculated using multiple sequence alignment by CLUSTALW www.genome.jp/tools/clustalw/ as a method to evaluate the similarity between two sequences. The calculation is summation of (1) K-tuple size, (2) gap penalty, (3) top diagonals, and (4) window size. Alignment score of two identical sequences of LDKA is 69 and the lowest alignment score in the APD is −49. Alignment score equals or is above 15 counts as the sequences are similar. $\Delta G_{Interface}$ shows the free energy from water to POPC interface, and was estimated using Wimley-White Scale in MPEx software.

As shown in Table 10, in-vitro experiments of LDKA analogues show their minimum inhibitory concentration with E. coli, S. aureus, and P. aeruginosa, and hemolysis assay with red blood cell shows their hemolytic activity at the corresponding peptide concentrations. $LC_{50}$ represents the lethal peptide concentration that causes 50% lysis of red blood cell. 75 μM peptide concentrations were the maximum concentration that was tested. "NDA" means "not determinable".

This approach helped us to identify how minor variations of a common sequence template result in dramatic differences in pore size, bilayer affinity, and bilayer selectivity, and antimicrobial activity.

Example 5

Rational Peptide Design.

Figure 10A:
FIGS. 10A-10E Design of the LDKA library that contains 2,916 variants. (10A) Amino acid sequence of LDKA (SEQ ID NO: 3) and its variants in the combinatorial library. (10B) Helical wheel projection of LDKA (SEQ ID NO: 3) shows charged and hydrophobic faces of the helix, which assumes it's a completely helical configuration. Red and blue symbols present charged residues: negative charged and positive charged, respectively. Proline acts as a kink in the helix, and it's shown as green symbols. Other hydrophobic (leucine) and small (glycine and alanine) residues are indicated as gray symbols. (10C) High-throughput screen of LDKA library induces leakage of fluorescent dye (ANTS/DPX) entrapped in each POPC (x-axis) and POPG (y-axis) vesicles. Small fluorescent dye (~400 Da) release above 90% from each POPC and POPG vesicles are highlighted in green areas, and are selected to further analyze their pore sizes using a macromolecular fluorescent dye (3-kDa dextran). Pore-size characterization of selected LDKA library variants cause 3-kDa dextran releasing from each (10D) POPC and (10E) POPG vesicles.

LDKA is a good general pore-former in neutral POPC and charged POPG vesicles and has low micromolar antimicrobial activity against bacteria, which is similar to many natural potent AMPs. The goal of this library is to explore if simple rearrangements of the LDKA sequence, using the same four amino acids (L,D,K,A), will allow modulation of (i) pore-forming potential, (ii) pore-size, and (iii) targeting of specific membrane types. To achieve this, we design a peptide library containing 2,916 LDKA analogues (FIG. 10a) that introduce systematic mutations into the LDKA template sequence in order to: (1) adjust peptide hydrophobicity, (2) add more charged residues, (3) introduce a central proline residue, and (5) substitute more positively charged residues onto the C-terminus.

Figure 10B:
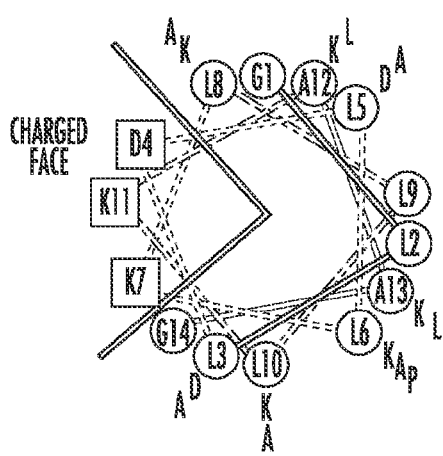

Peptide hydrophobicity is modulated by interchanging leucine and alanine residues as well as introducing positive (lysine) and negative charges (aspartic acid) at additional positions along the sequence. The goal of these mutations is to tune the solubility and membrane-partitioning strength of the peptide. A proline, which is thought to aid with solubility and structural plasticity of the peptide, is introduced near the centre of the sequence as many AMPs have this feature. The goal of the additional charges (Asp and Lys) is to both facilitate inter-peptide salt-bridge formation to strengthen the peptide-peptide interface, as well as to allow for a more polar central pore enabling larger multimeric channel structures (FIG. 10b). Additional positive charges are introduced at the C-terminus to enhance peptide binding to anionic lipids, which are more common in bacterial membranes. The C-terminus was chosen for the extra positive charges following analyses of known AMPs, many of which have positively charged C-termini (e.g. Hylain 2,[26] melittin,[34,35] and maculatin[36,37]).

In addition to the peptide library we also designed a single LDKA analog that replaces the central lysine of the LDKA wildtype (WT) with a histidine. This mutant was motivated by several studies proposing that polar histidines may aid with pore assembly of AMPs.[17] We therefore synthesized this K7H mutant.

TABLE 7

Peptide solubility test of LDKA and its mutants. Solubility test was provided by the distributor, GenScript USA Inc. DMSO: dimethyl sulfoxide (analytical grade). DPBS: Dulbecco's phosphate buffered saline, containing potassium chloride (KCl), potassium phosphate monobasic ($KH_2PO_4$), sodium chloride (NaCl) and sodium phosphate diabsic ($Na_2HPO_4 \cdot 7_{H_2}O$). Blue text means the inventors tested the solubility and revised number. †N-terminus is free, C-terminus: -NH2. ‡Large pore for PG only.

| Pore Size | LDKA | Peptide | Sequence† | M.W. | Ultrapure Water [mg/mL] | DPBS pH 7.1 [mg/mL] | DMSO [mg/mL] |
|---|---|---|---|---|---|---|---|
| PG>PC | Large‡ | WT | GLLDLLKLLLKAAG-$CO_2^-$ (SEQ ID NO: 1) | 1438 | 10 | <0.1 | 20 |
| — | — | K7H | GLLDLLHLLLKAAGW (SEQ ID NO: 4) | 1632 | 1 | <0.1 | 15 |

TABLE 7-continued

Peptide solubility test of LDKA and its mutants. Solubility test was provided by the distributor, GenScript USA Inc. DMSO: dimethyl sulfoxide (analytical grade). DPBS: Dulbecco's phosphate buffered saline, containing potassium chloride (KCl), potassium phosphate monobasic KH$_2$PO$_4$), sodium chloride (NaCl) and sodium phosphate diabsic (Na$_2$HPO$_4$-7$_{H2}$O). Blue text means the inventors tested the solubility and revised number. †N-terminus is free, C-terminus: -NH2. ‡Large pore for PG only.

| | Pore Size | LDKA Peptide | Sequence† | M.W. | Ultrapure Water [mg/mL] | DPBS pH 7.1 [mg/mL] | DMSO [mg/mL] |
|---|---|---|---|---|---|---|---|
| Non-selective | Small | 7F3 | GADLAKLLLKLLGW (SEQ ID NO: 5) | 1623 | 5 | <0.1 | 15 |
| | Large | 28H6 | GLLDLLKLLLKLAGW (SEQ ID NO: 6) | 1665 | 0.5 | <0.1 | 15 |
| | Large‡ | 25B2 | GLDDLAKLLLKLAGW (SEQ ID NO: 7) | 1625 | 10 | <0.1 | 15 |
| PC > PG | Small | 4H9 | GLDDLLKALLKAAGW (SEQ ID NO: 8) | 1583 | 5 | 10 | 15 |
| PG > PC | Small | 7D12 | GLLLDAKLLAKLAGW (SEQ ID NO: 9) | 1583 | 10 | <0.1 | 20 |
| | Small | 7G6 | GLLDLPKALAKALGW (SEQ ID NO: 10) | 1565 | 10 | 15 | 15 |
| | Large | 11D12 | GLADAAKLLLKAAGW (SEQ ID NO: 11) | 1497 | 10 | 10 | 20 |
| | Large | 24F1 | GLLDAAKLLAKAAGW (SEQ ID NO: 12) | 1497 | 10 | 5 | 15 |

Example 6

Membrane Specific Poration.

Figure 10C:
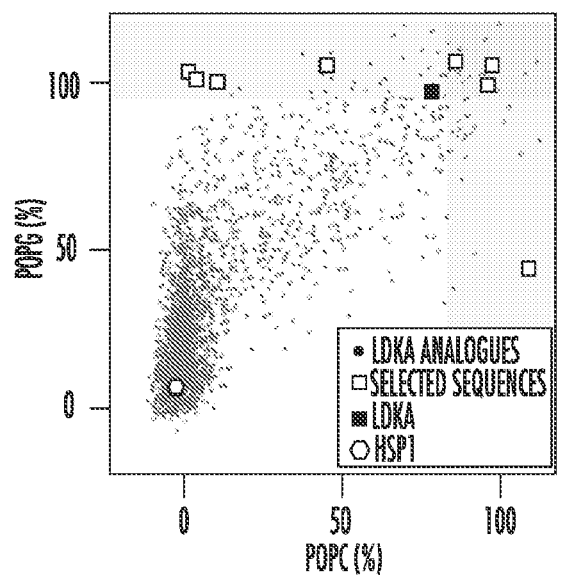

The selectivity of the 2,916 LDKA library peptides for zwitterionic (POPC) and anionic (POPG) unilamellar vesicles (LUVs) was determined using a high-throughput fluorescent dye leakage screen. This detects and quantifies the release of a small fluorescent dye (ANTS/DPX; MW=~400 Da) encapsulated in LUVs after addition of library peptides. Neutral POPC LUVs serve as a simple model for mammalian membranes, while charged POPG LUVs mimic bacterial membranes enriched in anionic lipids. FIG. 10c shows the fraction of fluorescent dye leakage from both neutral and charged LUVs after addition of library peptides. Of the LDKA analogs that result in more than 50% leakage of encapsulated dye, 11.2% of them only porate charged POPG vesicles, while 0.4% cause leakage from neutral POPC vesicles only, and 6.6% disrupt both vesicles.

TABLE 8

| Pore Size | | LDKA Peptide | T [° C.] | Peptide-only [Helix/Strand] | Peptide-POPC [Helix/Strand] | Peptide-POPG [Helix/Strand] |
|---|---|---|---|---|---|---|
| — | — | WT | 20 | 54/5 | 68/3 | 90/0 |
| | | | 45 | — | 63/3 | 82/2 |
| | | | 70 | — | 54/5 | 75/4 |
| | | | 95 | — | 48/9 | 60/8 |
| — | — | K7H | 20 | 62/4 | 65/5 | 53/11 |
| | | | 45 | — | 80/1 | 59/8 |
| | | | 70 | — | 80/2 | 77/2 |
| | | | 95 | — | 72/3 | 77/2 |
| Non-selective | Small | 7F3 | 20 | 75/4 | 82/1 | 52/12 |
| | | | 45 | — | 77/2 | 58/7 |
| | | | 70 | — | 76/3 | 66/2 |
| | | | 95 | — | 70/4 | 76/2 |
| | Large | 28H6 | 20 | 63/4 | 58/10 | 18/32 |
| | | | 45 | — | 64/6 | 23/29 |
| | | | 70 | — | 68/6 | 27/25 |
| | | | 95 | — | 65/3 | 55/7 |
| | Large (PG) | 25B2 | 20 | 67/3 | 80/3 | 98/0 |
| | | | 45 | — | 90/1 | 98/0 |
| | | | 70 | — | 81/1 | 93/0 |
| | | | 95 | — | 61/6 | 87/1 |
| | Large (PC) | N/A | — | — | — | — |
| PC > PG | Small | 4H9 | 20 | 63/2 | 82/0 | 93/0 |
| | | | 45 | — | 77/0 | 91/0 |
| | | | 70 | — | 66/4 | 83/0 |
| | | | 95 | — | 47/11 | 73/1 |
| | Large | N/A | — | — | — | — |

TABLE 8-continued

| | Pore Size | LDKA Peptide | T [° C.] | Peptide-only [Helix/Strand] | Peptide-POPC [Helix/Strand] | Peptide-POPG [Helix/Strand] |
|---|---|---|---|---|---|---|
| PG > PC | Small | 7D12 | 20 | 38/11 | 30/20 | 78/2 |
| | | | 45 | — | 26/21 | 66/3 |
| | | | 70 | — | 27/22 | 48/6 |
| | | | 95 | — | 22/24 | 31/13 |
| | Small | 7G6 | 20 | 22/10 | 49/10 | 86/2 |
| | | | 45 | — | 56/6 | 87/2 |
| | | | 70 | — | 47/10 | 82/3 |
| | | | 95 | — | 30/20 | 75/3 |
| | Large | 11D12 | 20 | 32/8 | 38/12 | 96/0 |
| | | | 45 | — | 39/10 | 92/0 |
| | | | 70 | — | 39/9 | 90/0 |
| | | | 95 | — | 33/12 | 77/1 |
| | Large | 24F1 | 20 | 29/14 | 32/16 | 91/0 |
| | | | 45 | — | 32/16 | 88/1 |
| | | | 70 | — | 27/17 | 77/1 |
| | | | 95 | — | 24/22 | 66/2 |

Dichroweb software analyzes the secondary structure of LDKA peptides from circular dichroism spectroscope. The table presents the percentage of each helix and strand structure at different temperature. The data are analyzed using CONTIN-LL method and Reference Set 4 (Optimised for 190-240 nm).

Example 7

Pore Size.

Figure 10D:
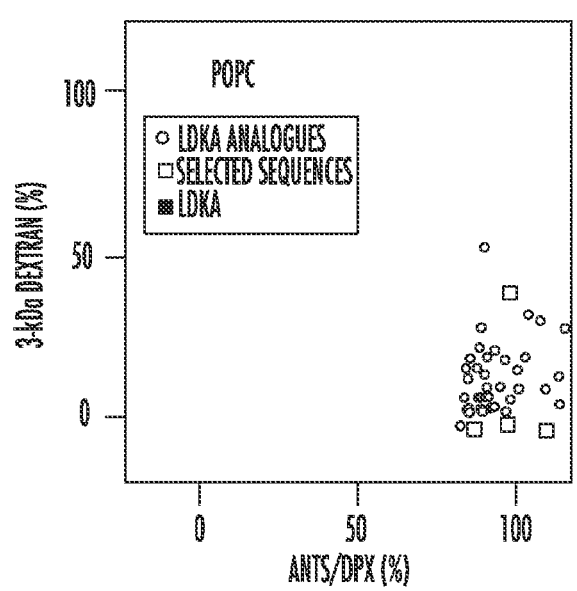
Figure 10E:
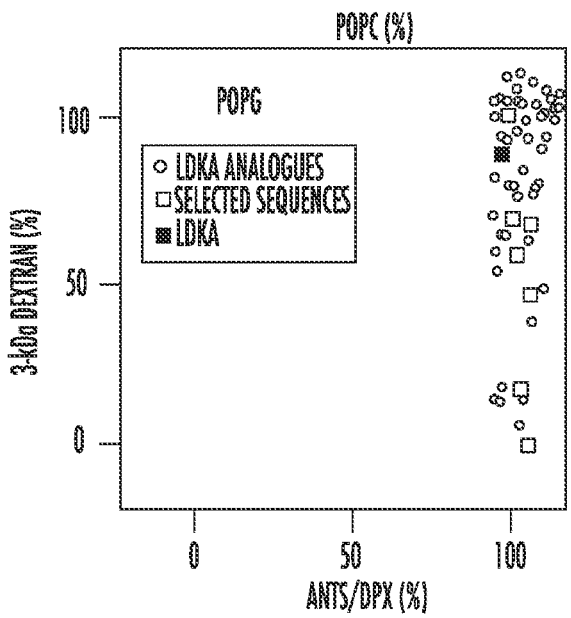

LDKA analogs that induce more than 90% dye leakage from POPC and POPG LUVs were screened for their ability to induce leakage of a larger 3-kDa TAMRA-biotin-dextran (TBD)[7] dye. FIGS. 10d and 10e (1d and 1e) show that of the small-dye leakage inducing peptides several form larger pores in POPG, while the pores induced in POPC are generally smaller.

Example 8

LDKA Analog Selection and Characterization.

Eight LDKA peptides with different lipid selectivity and pore sizes were selected from the high-throughput screen and sequenced. Table 9 shows that these peptides contain between 1 and 4 mutations compared to the LDKA template sequence. The most common mutation is L to A, occurred 13 times and in 7 out of the 8 peptides, followed by A to L, which occurred 6 times in 5 peptides, L to D which occurred 3 times in 3 peptides, and L to P that occurred once. Lysine (K) is not favorable to be shown at the position 6, 8, 10, 12, and 13, which is the non-polar face of the helical structure. It suggests that hydrophobic leucine and alanine are more preferable in this motif to support the helical structure in short peptide length. Remarkably, Table 9 reveals that L to A mutations are generally sufficient to prevent poration of neutral POPC membranes, resulting in peptides that porate charged POPG membranes only. More specifically, the analogs only induce leakage from anionic POPG vesicles have 4-5 leucines, which is less than the analogs that can porate both POPC and POPG vesicles and have 6-7 leucines in their sequences. The net charge of the LDKA WT and all analogs are between +1 and +2. We did not observe any anionic or neutral peptide, or peptide that has more than +2 net charge.

TABLE 9

LDKA and its selected variants induce fluorescent dyes (ANTS/DPX and 3-kDa) release from each POPC and POPG vesicles with P:L = 1:1000 at pH 7 phosphate buffer. †N-terminus is free, C-terminus: -NH2. ‡Large pore for PG only.

| | | | | ANTS/DPX | | 3-kDa Dextran | | | Hydro- |
|---|---|---|---|---|---|---|---|---|---|
| | Pore size | LDKA | Sequence† | POPC [%] | POPG [%] | POPC [%] | POPG [%] | Charge | phobic moment |
| PG > PC | Large‡ | WT | GLLDLLKLLLKAAG (SEQ ID NO: 1) | 81 | 97 | 22 | 89 | +1 | 4.24 |
| — | — | K7H | GLLDLLHLLLKAAGW (SEQ ID NO: 4) | — | — | — | — | +1 | 2.96 |
| Non-selective | Small | 7F3 | GLADLAKLLLKLLGW (SEQ ID NO: 5) | 88 | 106 | -3 | 46 | +2 | 4.15 |
| | Large | 28H6 | GLLDLLKLLLKLAGW (SEQ ID NO: 5) | 99 | 105 | 38 | 67 | +2 | 3.41 |
| | Large‡ | 25B2 | GLDDLAKLLLKLAGW (SEQ ID NO: 7) | 98 | 99 | -2 | 100 | +1 | 4.78 |
| PC > PG | Small | 4H9 | GLDDLLAALLKAAGW (SEQ ID NO: 8) | 110 | 43 | -4 | — | +1 | 4.09 |

TABLE 9-continued

LDKA and its selected variants induce fluorescent dyes (ANTS/DPX and 3-kDa) release from each POPC and POPG vesicles with P:L = 1:1000 at pH 7 phosphate buffer. †N-terminus is free, C-terminus: -NH2. ‡Large pore for PG only.

| Pore size | LDKA | Sequence† | ANTS/DPX POPC [%] | ANTS/DPX POPG [%] | 3-kDa Dextran POPC [%] | 3-kDa Dextran POPG [%] | Charge | Hydro-phobic moment |
|---|---|---|---|---|---|---|---|---|
| PG > PC | Small | 7D12 | GLLLDAKLLAKLAGW (SEQ ID NO: 9) | 6 | 103 | — | 17 | +2 | 1.92 |
| | Small | 7G6 | GLLDLPKALAKALGW (SEQ ID NO: 10) | 48 | 105 | — | -1 | +2 | 3.32 |
| | Large | 11D12 | GLADAAKLLLKAAGW (SEQ ID NO: 11) | 8 | 101 | — | 58 | +2 | 2.55 |
| | Large | 24F1 | GLLDAAKLLAKAAGW (SEQ ID NO: 12) | 15 | 100 | — | 69 | +2 | 2.35 |

Example 9

Secondary Structure and Membrane Partitioning.

To investigate the root cause of the different poration preferences of LDKA analogs for POPC and POPG membranes, we investigated the binding and secondary structural properties of LDKA analogs using circular dichroism (CD) spectroscopy. Peptide solutions (peptide concentration is 50 µM) were titrated with POPC and POPG LUVs (50, 100, 250, 500, 1000 µM) and the corresponding changes CD spectra collected. Analysis of these spectra using CD tools and Dichroweb provides an ensemble average of the changes in secondary structure in the presence of POPC and POPG LUVs (dichroweb.cryst.bbk.ac.uk), which gives a direct measure of the binding free energies for each peptide.

Example 10

Binding to Mixed Membranes.

To further investigate why some peptides (i.e. 7D12, 7G6, 11D12, 24F1, and 28H6) show selectivity for membrane types we measured peptide binding and secondary structural changes to vesicles containing binary mixtures of POPC and POPG lipids. FIGS. 10a-10e show the changes in the CD and tryptophan fluorescence spectra for these peptides upon addition of LUVs for whom the ratio of POPG was elevated from 0 to 100%. This reveals that analogs that are sensitive to the anionic POPG lipid and have significant structural changes with small PG ratios (20% POPG), except 7D12. Consistent with the POPC/POPG leakage assay, these lipid selective peptides show little or no binding to POPC, which bind strongly to POPG. It reveals that binding is associated to helical folding, except for 28H6. Interestingly, the intrinsically disordered peptide 28H6 shows tryptophan fluorescence with a spectral maximum of 331 nm in phosphate buffer, suggesting aggregate formation. All other peptides have tryptophan fluorescence peaks around 350 nm, indicative of monomeric peptides. Addition of LUVs to 28H6 results in higher intensity and smaller width of the peak indicative of membrane binding. Remarkably, the CD spectra of 28H6 change from a helical aggregate in solution or POPC LUVs, to beta-strand conformations in the presence of anionic POPG lipids. Increasing the temperature of 28H6 with POPG vesicles can destabilize the beta-strand structure and reverse it to helix as the conformation of 28H6 with POPC (Table 8).

Example 11

Antibacterial Activity.

The antibacterial activity of LDKA analogs against *E. coli*, *S. aureus*, and *P. aeruginosa* were tested in vitro in nutritionally rich medium. LDKA WT inhibits growth of all three bacteria at micromolar peptide concentrations of a similar range to potent natural AMPs. Table 10 shows that all POPG selective peptides (7G6, 11D12, and 24F1) have antibacterial activity to against *E. coli* with 19-44 µM peptide concentration, except for 7D12, which has no activity against any of the three bacterial species tested here. None of the POPG-selective peptides inhibit *S. aureus* or *P. aeruginosa*, except for 24F1, which inhibits growth of *P. aeruginosa* at 66 µM. Instead, the non-selective peptides 7F3, 25B2, and 4H9 are potent inhibitors of growth for *E. coli* and *S. aureus*, but not *P. aeruginosa*. Surprisingly, K7H also has significant antibacterial activity against *S. aureus* with a MIC of 3 µM, but does not inhibit either *E. coli* or *P. aeruginosa*.

TABLE 10

Table 10. In vitro experiments of LDKA analogues show their minimum inhibitory concentration with *E. coli*, *S. aureus*, and *P. aeruginosa*, and hemolysis assay with red blood cell shows their hemolytic activity at the corresponding peptide concentrations.

| Pore size | LDKA | Minimum Inhibitory Concentration [µM] | | | | Hemolysis Assay |
|---|---|---|---|---|---|---|
| | | *E. coli* | *S. aureus* | MRSA | *P. aeruginosa* | $LC_{50}$ [µM] |
| PG > PC Large‡ | WT | 35 ± 9 | 10 ± 0 | 38 ± 9 | 66 ± 14 | 55.1 |
| — — | K7H | NDA | 3 ± 1 | 7 ± 0 | NDA | 2.3 |

TABLE 10-continued

Table 10. In vitro experiments of LDKA analogues show their minimum inhibitory concentration with E. coli, S. aureus, and P. aeruginosa, and hemolysis assay with red blood cell shows their hemolytic activity at the corresponding peptide concentrations.

|  | Pore size | LDKA | Minimum Inhibitory Concentration [μM] | | | | Hemolysis Assay LC$_{50}$ [μM] |
| --- | --- | --- | --- | --- | --- | --- | --- |
|  |  |  | E. coli | S. aureus | MRSA | P. aeruginosa |  |
| Non-selective | Small | 7F3 | 57 ± 28 | 3 ± 1 | 29 ± 7 | NDA | 1.1 |
|  | Large | 28H6 | NDA | NDA | NDA | NDA | 1.2 |
|  | Large‡ | 25B2 | 22 ± 0 | 11 ± 3 | NDA | NDA | 35.5 |
| PC > PG | Small | 4H9 | 33 ± 14 | 66 ± 16 | NDA | NDA | 56.6 |
| PG > PC | Small | 7D12 | NDA | NDA | NDA | NDA | — |
|  | Small | 7G6 | 19 ± 5 | NDA | NDA | NDA | — |
|  | Large | 11D12 | 44 ± 10 | NDA | NDA | NDA | — |
|  | Large | 24F1 | 38 ± 9 | NDA | NDA | 66 ± 16 | — |

LC$_{50}$ present the lethal peptide concentration lysing 50% of red blood cells. The values are estimated using polynomial regression. 75 μM peptide concentration is the maximum amount tested.
"NDA" means "not determinable".
‡Large pore for PG only.

Example 12

Activity Against Antibiotic-Resistant Strains.

Figures 14A, 14B:
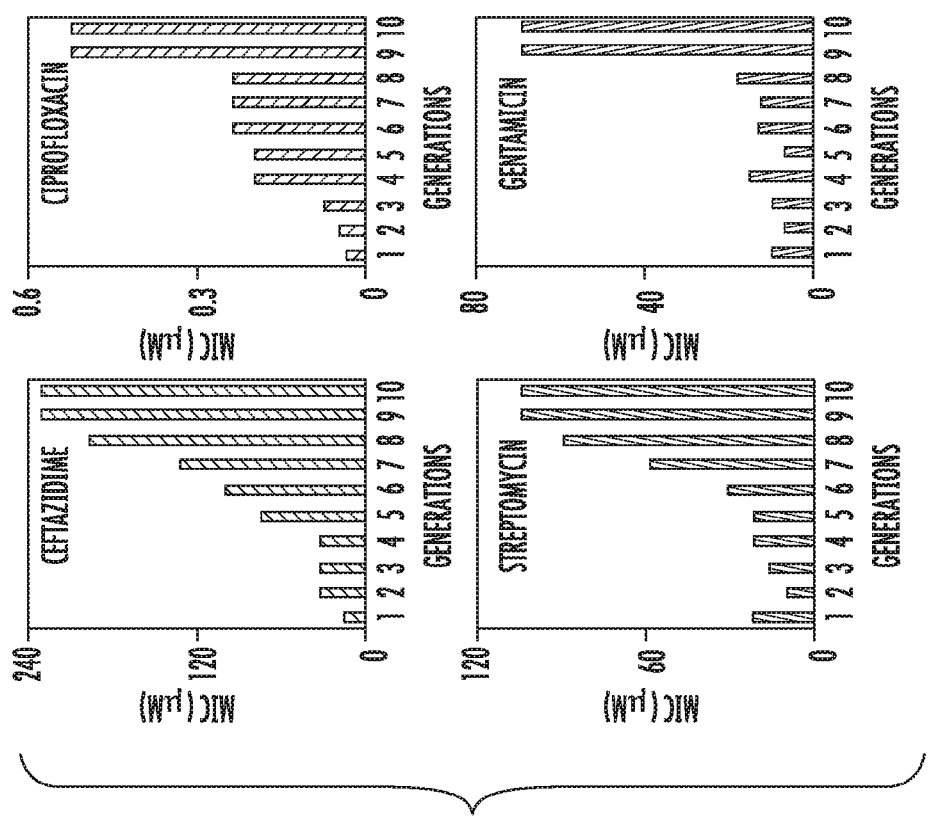
FIGS. 14A-14B LDKA analogues against drug resistant E. coli. (14A) Minimum inhibitory concentrations (MICs) of four antibiotics (eftazidime, ciprofloxacin, streptomycin, and gentamicin) treat serial E. coli generations. The E. coli that survives below/near the MICs was selected for the next generation. (14B) MICs of LDKA analogues against four different strains of drug resistant E. coli. "N.D." means "not determined".

Ceftazidime is active on the bacteria's cell wall and interferes with bacterial cell wall formation.[38,39] Ciprofloxacin is able to inhibit DNA gyrase, type II topoisomerase, and topoisomerase IV to separate bacterial DNA and inhibits cell division.[40] Streptomycin and gentamicin are antibiotics that can interrupt and inhibit protein synthesis.[41,42] E. coli strain ATCC 25922 cultures were grown in the presence of each of these antibiotics at elevated concentration for 10 generations. This resulted in a 4 to 16-fold resistance to these antibiotics compared to the 1$^{st}$ generation strain (FIG. 14a).

LDKA analogues were tested for their antibacterial activity against these four drug-resistant E. coli cultures. FIG. 14b shows that membrane-selective analogs (7G6, 11D12, and 24F1) remain effective and consistently inhibit the ceftazidime, streptomycin, and gentamicin-resistant E. coli strains with 27-44 μM peptide concentrations but need 67-150 μM against ciprofloxacin-resistant E. coli. Non-selective peptides (4H9, 7F3, and 25B2) are effective against ceftazidime-resistant and gentamicin-resistant E. coli at very low 6-14 μM peptide concentrations. However, these peptides require significantly higher peptide concentration (87-150 μM) against streptomycin-resistant E. coli, and completely fail against ciprofloxacin-resistant strains.

Example 13

Activity Against Biofilms.

Figure 13A:
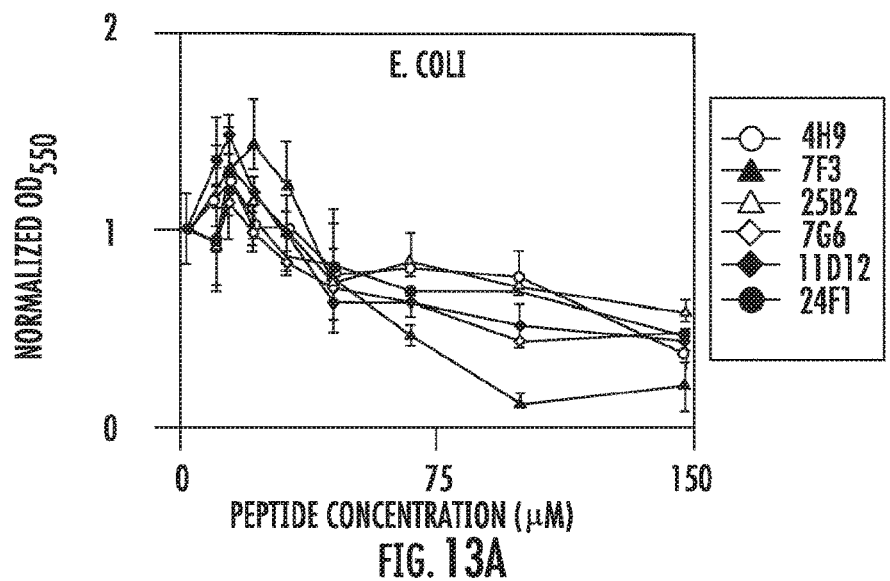
FIGS. 13A-13C Antibacterial activity of LDKA analogues against quantitative biofilm formation on polystyrene 96-well plate for 3 hr treatment. Selected analogues were tested with each (13A). Escherichia coli biofilm, (13B). Staphylococcus aureus biofilm, and (13C) Pseudomonas aeruginosa biofilm.
Figure 13B:
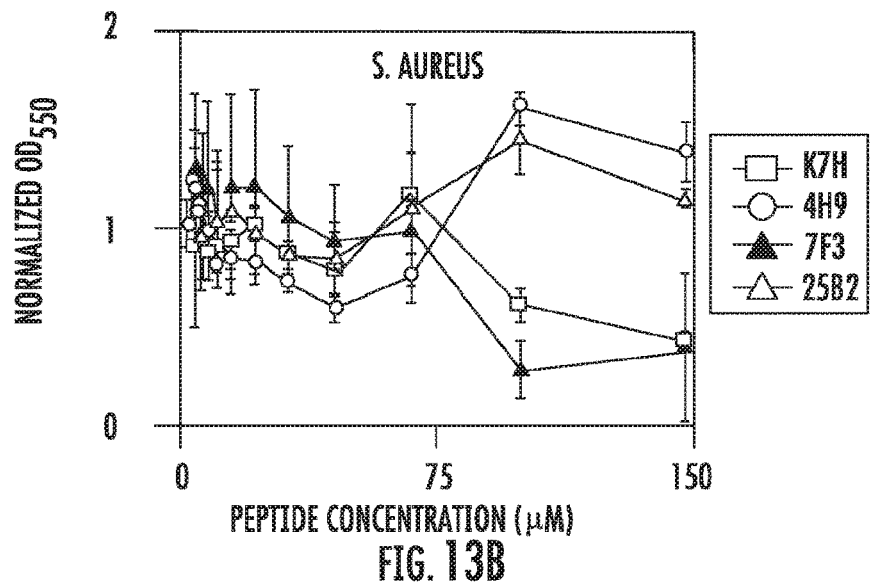
Figure 13C:
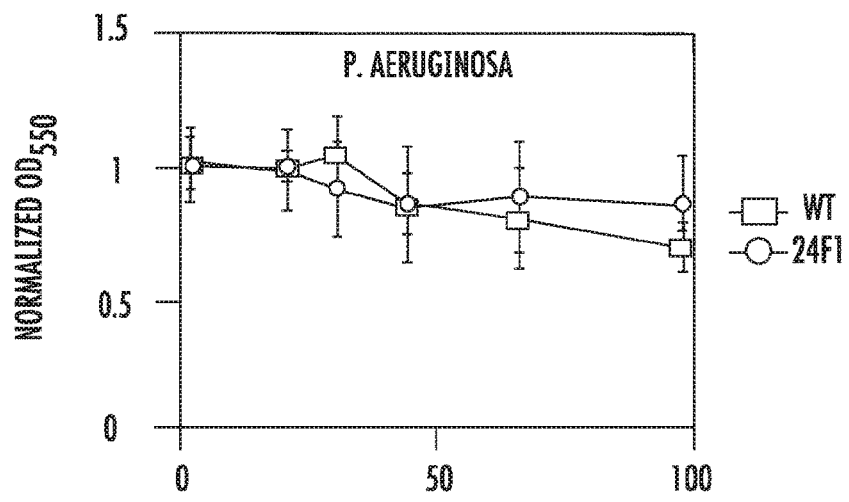

In clinical settings bacteria are mostly found in biofilms that are the key drivers of infections.[43,44] We therefore tested our LDKA analogs on bacterial biofilms, which are generally much more difficult to kill than their planktonic equivalents.[45] It shows that the selected LDKA analogues (4H9, 7F3, 25B2, 7G6, 11D12, and 24F1), which can inhibit the growth of planktonic E. coli, can elimintate ~50% of the E. coli biofilm in the presence of 67-150 μM peptide. However, most of the LDKA analogues fail to treat S. aureus and P. aeruginosa biofilms. Only K7H and 7F3 are capable to reduce S. aureus biofilms by ~50% with 100 μM peptide concentration, and none of the analogues work against P. aeruginosa biofilms (FIGS. 13a-13c).

Example 14

Hemolysis.

To test basic toxicity of the LDKA analogs we performed a hemolysis assay. LDKA WT is hemolytic at medium micromolar concentrations with an LC$_{50}$ of 55.1 μM (Table 10). We also found that K7H, 7F3, and 28H6 are significantly haemolytic, but do not harm any of the bacteria studied here.

Example 15

Isothermal Titration Calorimetry.

Figure 11:
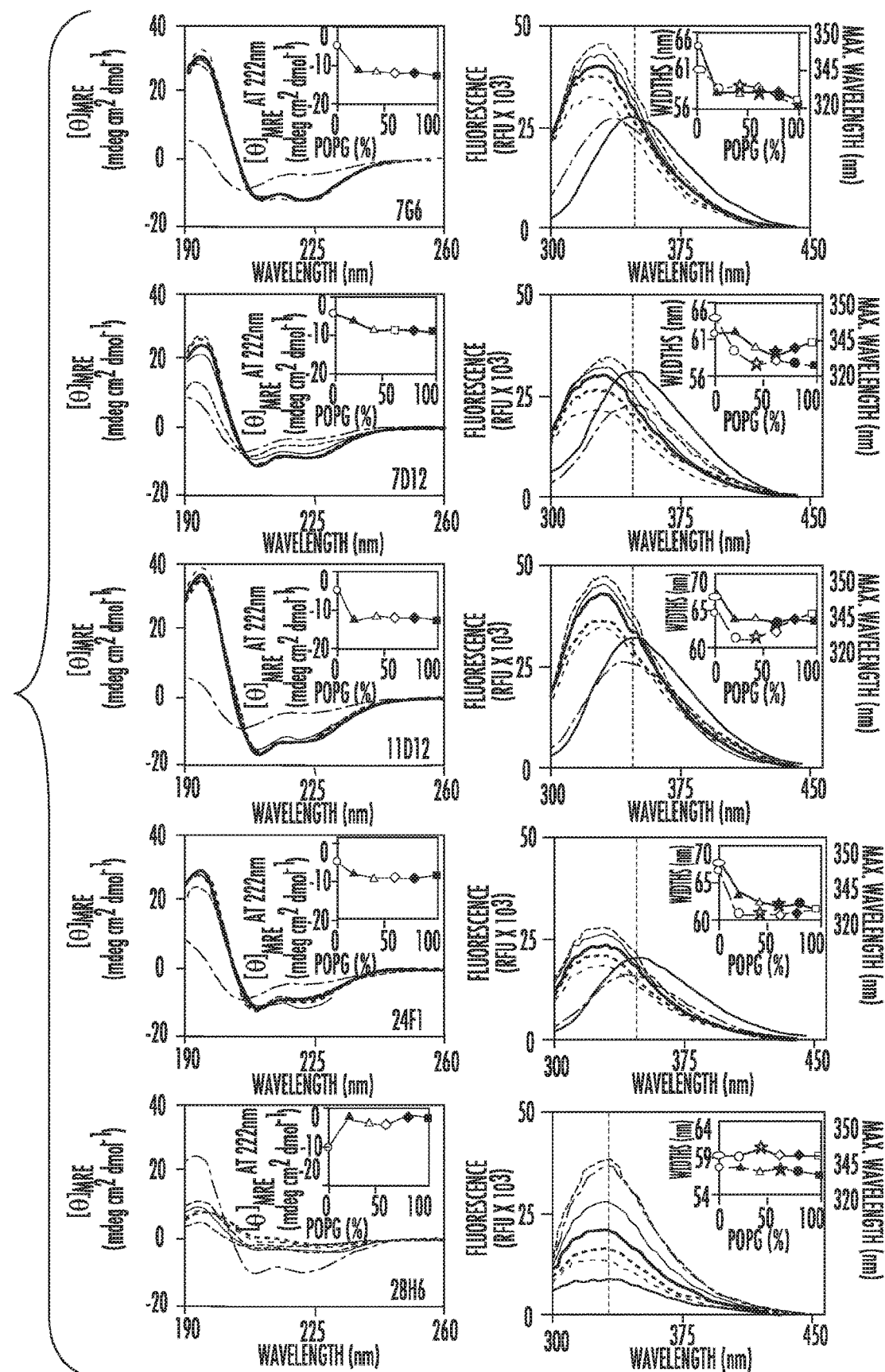
FIG. 11 Circular dichroism spectroscopy and tryptophan fluorescent binding assays show secondary structure and binding changes of LDKA analogs to vesicles containing binary mixtures of POPC and POPG lipids with P:L=1:12.
Figure 15A:
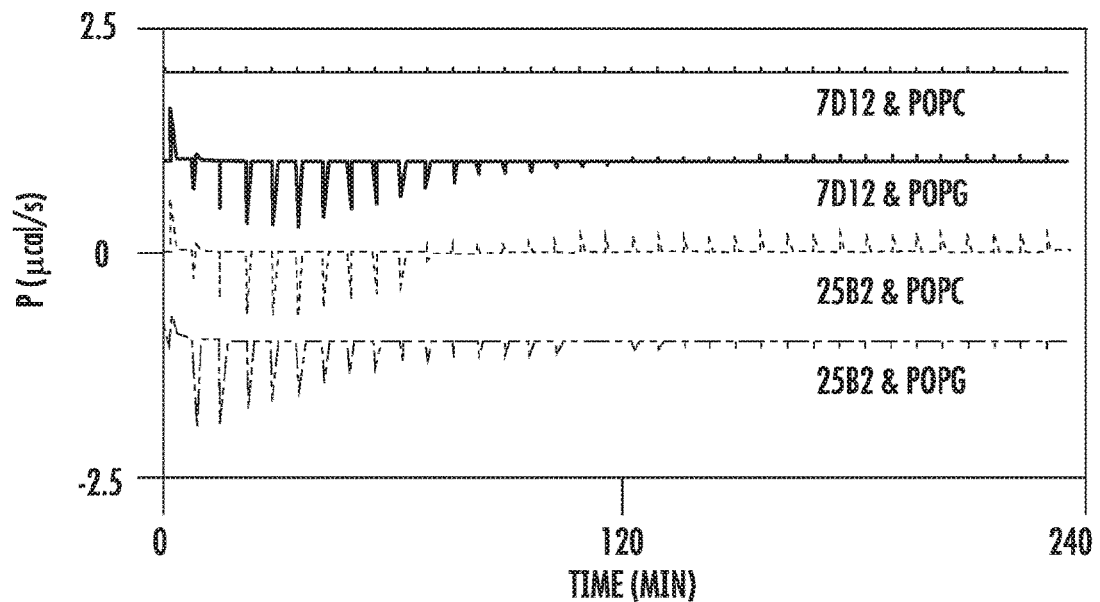
FIGS. 15A-15B Isothermal titration calorimetry shows (15A) heat released/absorbed upon interaction of the peptide (7D12 and 25B2) and titrated lipid (POPC and POPG) vesicles and (15B) thermodynamic parameters (e.g. stoichiometry, enthalpy, entropy of binding, and free energy).
Figure 15B:
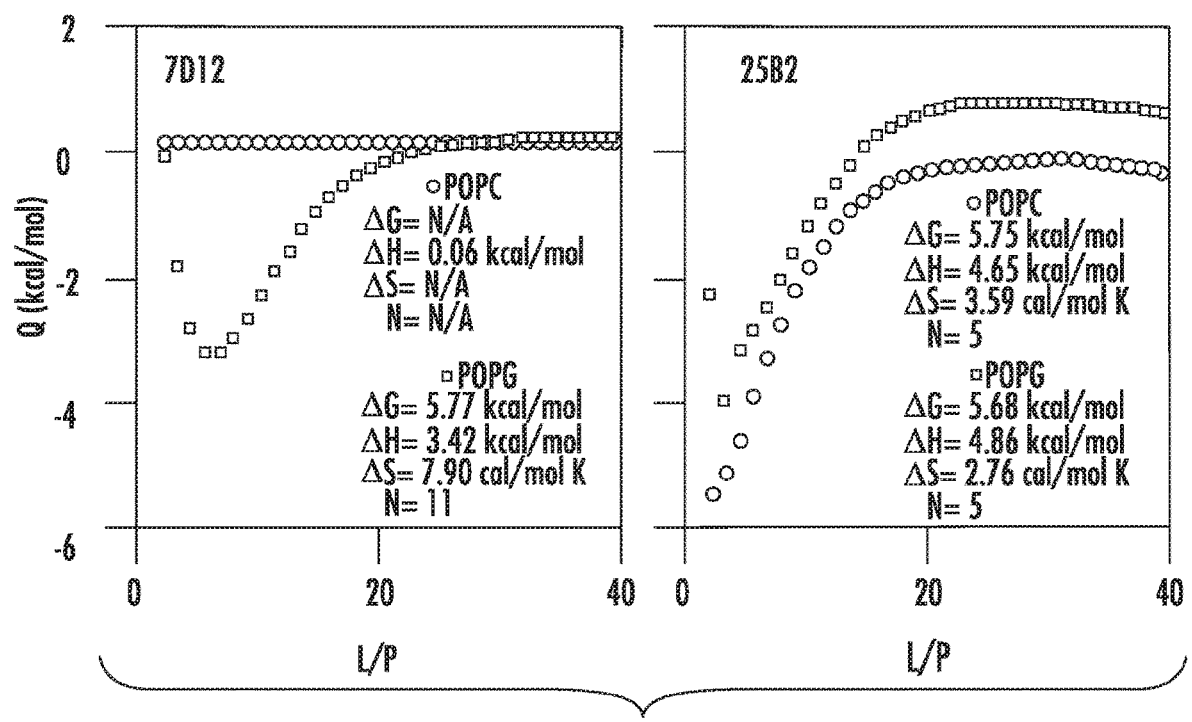

7D12 (sequence: GLLDDAKLLAKLAGW-Amide (SEQ ID NO: 9) and 25B2 (sequence: GLDDLAKLLLKLAGW-Amide (SEQ ID NO: 7)) share similar peptide sequences and have same net charge (+1) but result in completely different properties. 7D12 only porates POPG vesicle without damaging POPC vesicles, and 25B2 causes leakage from both neutral and charged vesicles. To understand why these minor modifications result in different functions, we applied isothermal titration calorimetry to further characterize their thermodynamic parameters (FIG. 15a-15b), e.g. stoichiometry (N) and enthalpy (ΔH). Titrating POPC vesicle into 7D12 results in ΔH=0.1 kcal/mol and we have confirmed 7D12 does not bind onto POPC using tryptophan fluorescent binding assay (FIG. 11). It suggests that this heat absorbed is caused by the solution mixing between peptide solution in chamber and titrated lipid solution. The titration of POPG vesicle in 7D12 has ΔH=−3.4 kcal/mol with N=11 lipids per peptide. On the other hand, 25B2 with titrated POPC and POPG show ΔH=−4.7 kcal/mol and ΔH=−4.9 kcal/mol, respectively, and they both have the same N=5 lipids per peptide. The ΔΔH between 25B2 in POPC and 25B2 in POPG is −0.21 kcal/mol, which may be the ion pairing (electrostatic) interaction between the positively charged residues on the peptide and anionic lipid (POPG) headgroup. The free energy of 7D12 in POPG, 25B2 in POPC, and 25B2 in POPG are determined using their binding affinity and ΔG=RT ln K$_d$, and the values are ~5.7 kcal/mol, which are similar. It implies that the change of entropy of 7D12 in POPG (ΔS=7.9 cal/mol K) is higher than 25B2 in the membranes (ΔS=2.8-3.6 cal/mol K). It suggests the structure of 7D12 in POPG is more disordered than 25B2 in the membranes; therefore, highly disordered 7D12 with POPG involves more lipid interactions (N=12 lipids per peptide) than the less disordered 25B2 in the membranes (N=5 lipids per peptide).

Example 16

Hydrophobic Moment and Helicity.

To further understand why the sequences differ in binding properties, non-selective 25B2 and selective 7D12 were compared These peptides have similar sequences but have completely different binding selectivities. These peptides both have net charge of +1 and have same C-terminal motif (-$K_{11}LAGW_{15}$-Amide (amino acids 11 to 15 of SEQ ID NO. 7)). The only differences between these two peptides are: (1) aspartic acid shifts from position 3 in 25B2 to position 5 in 7D12, and (2) hydrophobic site of 10 where 25B2 is leucine and 7D12 is alanine. These simple modifications result in the hydrophobic dipole moment of 4.8 and 1.9 in 25B2 and 7D12, respectively, which has 2.9 difference between their hydrophobic moments. Lower hydrophobic moment of 7D12 corresponds to less thermostable helical structure than others (data not shown) and reveals its unfolded and coiled structure is more disordered than the helical structure 25B2 compared to what we observed from isothermal titration calorimetry. The net charge of 25B2 and 7D12 are same, which is +1. Therefore, it suggests hydrophobic moment is the major factor to promote the membrane selectivity difference between these two peptides.

The linear regression analysis shows good agreement between hydrophobic moment, helicity in POPC, and leakage fraction from POPC vesicles. Interestingly, the hydrophobic moment of K7H is only 3.0, which is significantly lower than most of the non-selective LDKA analogs and their hydrophobic moments are between 3.4 and 4.8, whereas the hydrophobic moments of cell-selective analogs are between 1.9 and 3.3. The R-squared of linear regression analysis between hydrophobic moment and ANTS leakage fraction from POPC is 0.80 (FIG. 16a). It reveals the interaction between peptide and POPC is strongly dependent on the hydrophobic moment; however, the regression analysis shows the pore size in POPC does not correlate to the hydrophobic moment. FIGS. 16a-16d show that the helicity of a peptide is linearly correlated to the leakage fraction ($R^2$=0.86) confirming higher helical peptides have better penetration into the membrane and further promote pore formation or membrane disruption to cause leakage. The analogs that are potent to induce fluorescent dye leakage from zwitterionic POPC vesicle have >60% helical structure in the solution, include LDKA WT, 7F3, 28H6, 25B2, and 4H9, whereas the mutants that have membrane selectivity (7D12, 7G6, 11D12, and 24F1) are mostly coiled. The presence of POPC vesicles further increases the helicity of these peptides, but not 28H6, which retains its helicity (FIGS. 10a-10e). The linear regression analysis shows that the helicities of these short peptides in POPC are strongly correlated to the hydrophobic moment ($R^2$=0.91), and the R-squared value of peptide in solution is 0.56 (FIG. 16b), where the surroundings are polar water molecules. Nearly all the analogues have higher helicity with POPG vesicles, but not 28H6, which surprisingly forms beta-strand structure with 32% fraction and may be an intrinsically disordered peptide. The elevated temperature of LDKA analogues with POPC vesicle at 95° C. reveals that the helical thermostability is correlated to the hydrophobic moment with a R-squared value of 0.63 (FIG. 16c), where intra-molecule interactions may further maintain the structural stability at higher temperature (data not shown).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1) Zasloff, M. (1987) Magainins, a class of antimicrobial peptides from *Xenopus* skin: isolation, characterization of two active forms, and partial cDNA sequence of a precursor. *Proc. Natl. Acad. Sci. U.S.A.*, 84(15), 5449-5453.
2) Lehrer, R. I., Barton, A., Daher, K. A., Harwig, S. S., Ganz, T. and Selsted, M. E. (1989) Interaction of human defensins with *Escherichia coli*. Mechanism of bactericidal activity. *J. Clin. Invest.*, 84(2), 553-561.
3) Yeaman, M. R. and Yount, N.Y. (2003) Mechanisms of antimicrobial peptide action and resistance. *Pharmacol Rev.*, 55(1), 27-55.
4) Wang, G., Li, X. and Wang, Z. (2015) APD3: the antimicrobial peptide database as a tool for research and education. *Nucleic Acids Research*, 44(D1), D1087-D1093. 5) Wiedman, G., Fuselier, T., He, J., Searson, P. C., Hristova, K. and Wimley, W. C. (2014) Highly efficient macromolecule-sized poration of lipid bilayers by a synthetically evolved peptide. *J. Am. Chem. Soc.*, 136 (12), 4724-4731.
6) Krauson, A. J., He, J. and Wimley, W. C. (2012) Gain-of-function analogues of the pore-forming peptide melittin selected by orthogonal high-throughput screening. *J. Am. Chem. Soc.*, 134(30), 12732-12741.
7) Krauson, A. J., Hall, O. M., Fuselier, T., Starr, C. G., Kauffman, W. B. and Wimley, W. C. (2015) Conforma- 8) Wiedman, G., Wimley, W. C. and Hristova, K. (20115) Testing the limits of rational design by engineering pH sensitivity into membrane-active peptides. *Biochim. Biophys. Acta,* 1848(4), 951-957.
9) Wiedman, G., Kim, S. Y., Zapata-Mercado, E., Wimley, W. C. and Hristova, K. (2017) pH-triggered, macromolecule-sized poration of lipid bilayers by synthetically evolved peptides. *J. Am. Chem. Soc.,* 139(2):937-945.
10) Sreedharan, J., Blair, I. P., Tripathi, V. B., Hu, X., Vance, C., Rogelj, B., Ackerley, S., Durnall, J. C., Williams, K. L., Buratti, E., Baralle, F., de Belleroche, J., Mitchell, J. D., Leigh, P. N., Al-Chalabi, A., Miller, C. C., Nicholson, G. and Shaw, C. E. (2008) TDP-43 mutations in familial and sporadic amyotrophic lateral sclerosis. *Science,* 319 (5870), 1668-1672.
11) Chen, A. K. H., Lin, R. Y. Y., Hsieh, E. Z. J., Tu, P., Chen, R. P. Y., Liao, T., Chen, W., Wang, C. and Huang, J. J. T. (2010) Induction of amyloid fibrils by the C-terminal fragments of TDP-43 in amyotrophic lateral sclerosis. *J. Am. Chem. Soc.,* 132(4), 1186-1187.
12) Liu, G. C., Chen, B. P., Ye, N. T., Wang, C. H., Chen, W., Lee, H. M., Chan, S. I. and Huang, J. J. (2013) Delineating the membrane-disrupting and seeding properties of the TDP-43 amyloidogenic core. *Chem. Commun.,* 49(95), 11212-11214.
13) Sun, C. S., Wang, C. Y., Chen, B. P., He, R. Y., Liu, G. C., Wang, C. H., Chen, W., Chern, Y. and Huang, J. J. (2014) The influence of pathological mutations and proline substitutions in TDP-43 glycine-rich peptides on its amyloid properties and cellular toxicity. *PloS One.* 9(8), e103644.
14) Chen, C. H., Khan, A., Huang, J. J. and Ulmschneider, M. B. (2016) Mechanisms of membrane pore formation by amyloidogenic peptides in amyotrophic lateral sclerosis. *Chem. Eur. J.,* 22(29), 9958-9961.
15) Grau-Campistany, A., Strandberg, E., Wadhwani, P., Reichert, J., Bürck, J., Rabanal, F. and Ulrich, A. S. (2015) Hydrophobic mismatch demonstrated for membranolytic peptides, and their use as molecular rulers to measure bilayer thickness in native cells. *Sci. Rep.,* 5, 9388.
16) Grau-Campistany, A., Strandberg, E., Wadhwani, P., Rabanal, F. and Ulrich, A. S. (2016) Extending the hydrophobic mismatch concept to amphiphilic membranolytic peptides. *J. Phys. Chem. Lett.,* 7(7), 1116-1120.
17) Wang, Y., Chen, C. H., Hu, D., Ulmschneider, M. B. and Ulmschneider, J. P. (2016) Spontaneous formation of structurally diverse membrane channel architectures from a single antimicrobial peptide. *Nat. Commun.,* 7, 13535.
18) Mishra, B. and Wang, G. (2012) Ab initio design of potent anti-MRSA peptides based on database filtering technology. *J. Am. Chem. Soc.,* 134(30), 12426-12429.
19) Wimley, W. C. and White, S. H. (1996) Experimentally determined hydrophobicty scale for proteins at membrane interfaces. *Nat. Struct. Biol.,* 3(10), 842-848.
20) Chen, C. H., Wiedman, G., Khan, A. and Ulmschneider, M. B. (2014) Absorption and folding of melittin onto lipid bilayer membranes via unbiased atomic detail microsecond molecular dynamics simulation. *Biochim. Biophys. Acta,* 1838(9), 2243-2249.
21) Ulmschneider, M. B., Ulmschneider, J. P., Schiller, N., Wallace, B. A., von Heijne, G. and White, S. H. (2014) Spontaneous transmembrane helix insertion thermodynamically mimics translocon-guided insertion. *Nat. Commun.,* 5, 4863.
22) Walther, T. H. and Ulrich, A. S. (2014) Transmembrane helix assembly and the role of salt bridges. *Curr. Opin. Struct. Biol.,* 27, 63-68.
23) Ulmschneider, M. B. and Ulmschneider, J. P. (2008) Folding peptides into lipid bilayer membranes. *J. Chem. Theory Comput.,* 4(11), 1807-1809.
24) Ulmschneider, J. P., Smith, J. C., White, S. H. and Ulmschneider, M. B. (2011) In silico partitioning and transmembrane insertion of hydrophobic peptides under equilibrium conditions. *J. Am. Chem. Soc.,* 133(39), 15487-15495.
25) Prates, M. V., Sforça, M. L., Regis, W. C., Leite, J. R., Silva, L. P., Pertinhez, T. A., Araújo, A. L., Azevedo, R. B., Spisni, A. and Bloch, C. Jr. (2004) The NMR-derived solution structure of a new cationic antimicrobial peptide from the skin secretion of the anuran *Hyla punctata*. *J. Biol. Chem.,* 279(13), 13018-13026.
26) Wu, J., Liu, H., Yang, H., Yu, H., You, D., Ma, Y., Ye, H. and Lai, R. (2011) Proteomic analysis of skin defensive factors of tree frog *Hyla simplex*. *J. Proteome Res.,* 10(9), 4230-4240.
27) Raftery, M. J., Waugh, R. J., Bowie, J. H., Wallace, J. C. and Tyler, M. J. (1996) The structures of the frenatin peptides from the skin secretion of the giant tree frog Litoria infrafrenata. *J. Pept. Sci.,* 2(2), 117-124.
28) Rozek, T., Wegener, K. L., Bowie, J. H., Olver, I. N., Carver, J. A., Wallace, J. C. and Tyler, M. J. (2000) The antibiotic and anticancer active aurein peptides from the Australian Bell Frogs Litoria aurea and Litoria raniformis the solution structure of aurein 1.2. *Eur. J. Biochem.* 267(17), 5330-5341.
29) Wegener, K. L., Brinkworth, C. S., Bowie, J. H., Wallace, J. C. and Tyler, M. J. (2001) Bioactive dahlein peptides from the skin secretions of the Australian aquatic frog Litoria dahlii: sequence determination by electrospray mass spectrometry. *Rapid Commun. Mass Spectrom.* 15(18), 1726-1734.
30) Jackway, R. J., Bowie, J. H., Bilusich, D., Musgrave, I. F., Surinya-Johnson, K. H., Tyler, M. J. and Eichinger, P. C. (2008) The fallaxidin peptides from the skin secretion of the Eastern Dwarf Tree Frog Litoria fallax. Sequence determination by positive and negative ion electrospray mass spectrometry: antimicrobial activity and cDNA cloning of the fallaxidins. *Rapid Commun. Mass Spectrom.,* 22(20), 3207-3216.
31) Steinborner, S. T., Bowie, J. H., Tyler, M. J. and Wallace, J. C. (1997) An unusual combination of peptides from the skin glands of ewing's tree frog, Litoria ewingi. Sequence determination and antimicrobial activity. *Aus. J. Chem.,* 50(9), 889-894.
32) Sitaram, N., Subbalakshmi, C. and Nagaraj, R. (2003) Indolicidin, a 13-residue basic antimicrobial peptide rich in tryptophan and proline, interacts with Ca(2+)-calmodulin. *Biochem. Biophys. Res. Commun.,* 309(4), 879-884.
33) San Mauro, D., Vences, M., Alcobendas, M., Zardoya, R. and Meyer, A. (2005) Initial diversification of living amphibians predated the breakup of Pangaea. *Am. Nat.,* 169 (5), 590-599.
34) Dempsey, C. E., Bazzo, R., Harvey, T. S., Syperek, I., Boheim, G. and Campbell, I.D. (1991) Contribution of proline-14 to the structure and actions of melittin. *FEBS Lett.,* 281(1-2), 240-244.
35) Rex, S. (2000) A Pro-->Ala substitution in melittin affects self-association, membrane binding and pore-formation kinetics due to changes in structural and electrostatic properties. *Biophys. Chem.,* 85(2-3), 209-228.

36) Fernandez, D. I., Lee, T. H., Sani, M. A., Aguilar, M. I. and Separovic, F. (2013) Proline facilitates membrane insertion of the antimicrobial peptide maculatin 1.1 via surface indentation and subsequent lipid disordering. *Biophys. J.,* 104(7), 1495-1507.
37) Sani, M. A., Lee, T. H., Aguilar, M. I. and Separovic, F. (2015) Proline-15 creates an amphipathic wedge in maculatin 1.1 peptides that drives lipid membrane disruption. *Biochim. Biophys. Acta,* 1848(10):2277-2289.
38) Richards, D. M. and Brogden, R. N. (1985) Ceftazidime. A review of its antibacterial activity, pharmacokinetic properties and therapeutic use. Drugs, 29(2), 105-161.
39) Yost R. L. and Ramphal R. (1985) Ceftazidime review. *Drug Intell. Clin. Pharm.,* 19(7-8), 509-13.
40) Drlica, K. and Zhao, X. (1997) DNA gyrase, topoisomerase IV, and the 4-quinolones. *Microbiol. Mol. Biol. Rev.,* 61(3):377-392.
41) Luzzatto, L., Apirion, D. and Schlessinger, D. (1968) Mechanism of action of streptomycin in *E. coli*: interruption of the ribosome cycle at the initiation of protein synthesis. *Proc. Natl. Acad. Sci. USA.,* 60(3), 873-880.
42) Hahn, F. E. and Sarre, S. G. (1969) Mechanism of action of gentamicin. *J. Infect. Dis.,* 203(1), 1-2.
43) Costerton, J. W., Stewart, P. S. and Greenberg, E. P. (1999) Bacterial biofilms: a common cause of persistent infections. *Science,* 284(5418), 1318-1322.
44) Hall-Stoodley, L., Costerton, J. W. and Stoodley, P. (2004) Bacterial biofilms: from the natural environment to infectious diseases. *Nat. Rev. Microbiol.,* 2(2), 95-108.
45) Stewart, P. S. and Costerton, J. W. (2001) Antibiotic resistance of bacteria in biofilms. *Lancet,* 358(9276), 135-138.

The invention claimed is:

1. A pore-forming, membrane-active peptide comprising the amino acid sequence GLLDLLKLLLKAAG (SEQ ID NO: 3), GLLDLLHLLLKAAGW-AMIDE (SEQ ID NO: 4), GLADLAKLLLKLLGW-AMIDE (SEQ ID NO: 5), GLLDLLKLLLKLAGW-AMIDE (SEQ ID NO: 6), GLDDLAKLLLKLAGW-AMIDE (SEQ ID NO: 7), GLDDLLKALLKAAGW-AMIDE (SEQ ID NO: 8), GLLDDAKLLAKLAGW-AMIDE (SEQ ID NO: 9), GLLDLPKALAKALGW-AMIDE (SEQ ID NO: 10), GLADAAKLLLKAAGW-AMIDE (SEQ ID NO: 11), or GLLDAAKLLAKAAGW-AMIDE (SEQ ID NO: 12), or a fusion polypeptide comprising an amino acid sequence of any of the above peptides.

2. The pore-forming, membrane-active peptide of claim 1, selected from the group consisting of: GLLDLLHLLL-KAAGW-AMIDE (SEQ ID NO: 4), GLADLAK-LLLKLLGW-AMIDE (SEQ ID NO: 5), GLLD-LLKLLLKLAGW-AMIDE (SEQ ID NO: 6), GLDDLAKLLLKLAGW-AMIDE (SEQ ID NO: 7), GLD-DLLKALLKAAGW-AMIDE (SEQ ID NO: 8), GLLD-DAKLLAKLAGW-AMIDE (SEQ ID NO: 9), GLLD-LPKALAKALGW-AMIDE (SEQ ID NO: 10), and GLADAAKLLLKAAGW-AMIDE (SEQ ID NO: 11), or a fusion polypeptide comprising an amino acid sequence of any of the above peptides.

3. A pore-forming, membrane-active peptide comprising the amino acid sequence of GXXDXXKXXXKXXGW-Amide (SEQ ID NO: 24), where x is independently any one of A, L, K, or D.

4. A method for treatment of a microbial infection in a subject in need thereof comprising administering to the subject an effective amount of a pore-forming, membrane-active peptide comprising the amino acid sequence of GLLDLLKLLLKAAG (SEQ ID NO: 3), GLLDLLHLLL-KAAGW-AMIDE (SEQ ID NO: 4), GLADLAK-LLLKLLGW- AMIDE (SEQ ID NO: 5), GLLD-LLKLLLKLAGW-AMIDE (SEQ ID NO: 6), GLDDLAKLLLKLAGW-AMIDE (SEQ ID NO: 7), GLD-DLLKALLKAAGW-AMIDE (SEQ ID NO: 8), GLLD-DAKLLAKLAGW-AMIDE (SEQ ID NO: 9), GLLD-LPKALAKALGW-AMIDE (SEQ ID NO: 10), GLADAAKLLLKAAGW-AMIDE (SEQ ID NO: 11), or GLLDAAKLLAKAAGW-AMIDE (SEQ ID NO: 12), or a fusion polypeptide comprising an amino acid sequence of any of the above peptides.

5. A method for treatment of a microbial infection in a subject in need thereof, comprising administering to the subject an effective amount of a pharmaceutical composition comprising one or more antimicrobial peptides comprising the amino acid sequence of GLLDLLKLLLKAAG (SEQ ID NO: 3), GLLDLLHLLLKAAGW-AMIDE (SEQ ID NO: 4), GLADLAKLLLKLLGW-AMIDE (SEQ ID NO: 5), GLLDLLKLLLKLAGW-AMIDE (SEQ ID NO: 6), GLDDLAKLLLKLAGW-AMIDE (SEQ ID NO: 7), GLDDLLKALLKAAGW-AMIDE (SEQ ID NO: 8), GLLDDAKLLAKLAGW-AMIDE (SEQ ID NO: 9), GLLDLPKALAKALGW-AMIDE (SEQ ID NO: 10), GLADAAKLLLKAAGW-AMIDE (SEQ ID NO: 11), or GLLDAAKLLAKAAGW-AMIDE (SEQ ID NO: 12), or a fusion polypeptide comprising an amino acid sequence of any of the above peptides, and a pharmaceutically acceptable carrier.

6. A method for treatment of a microbial infection in a subject in need thereof comprising administering to the subject an effective amount of a pharmaceutical composition comprising one or more antimicrobial peptides comprising the amino acid sequence of GLLDLLKLLLKAAG (SEQ ID NO: 3), GLLDLLHLLLKAAGW-AMIDE (SEQ ID NO: 4), GLADLAKLLLKLLGW-AMIDE (SEQ ID NO: 5), GLLDLLKLLLKLAGW-AMIDE (SEQ ID NO: 6), GLDDLAKLLLKLAGW-AMIDE (SEQ ID NO: 7), GLDDLLKALLKAAGW-AMIDE (SEQ ID NO: 8), GLLDDAKLLAKLAGW-AMIDE (SEQ ID NO: 9), GLLDLPKALAKALGW-AMIDE (SEQ ID NO: 10), GLADAAKLLLKAAGW-AMIDE (SEQ ID NO: 11), or GLLDAAKLLAKAAGW-AMIDE (SEQ ID NO: 12); or a fusion polypeptide comprising an amino acid sequence of any of the above peptides, at least one additional biologically active agent, and a pharmaceutically acceptable carrier.

7. A method of treating a surface to prevent or remove microbial growth comprising applying to the surface an effective amount of one or more antimicrobial peptides comprising the amino acid sequence of GLLDLLKLLLKAAG (SEQ ID NO: 3), GLLDLLHLLLKAAGW-AMIDE (SEQ ID NO: 4), GLADLAKLLLKLLGW-AMIDE (SEQ ID NO: 5), GLLDLLKLLLKLAGW-AMIDE (SEQ ID NO: 6), GLDDLAKLLLKLAGW-AMIDE (SEQ ID NO: 7), GLDDLLKALLKAAGW-AMIDE (SEQ ID NO: 8), GLLDDAKLLAKLAGW-AMIDE (SEQ ID NO: 9), GLLDLPKALAKALGW-AMIDE (SEQ ID NO: 10), GLADAAKLLLKAAGW-AMIDE (SEQ ID NO: 11), and GLLDAAKLLAKAAGW-AMIDE (SEQ ID NO: 12); or a fusion polypeptide comprising an amino acid sequence of any of the above peptides.

8. The method of claim 7, wherein said method further comprises at least one additional antimicrobial or disinfecting agent.

* * * * *

SEQUENCE LISTING

```
<160> NUMBER OF SEQ ID NOS: 30

<210> SEQ ID NO 1
<211> LENGTH: 14
<212> TYPE: PRT
<213> ORGANISM: Artificial Sequence
<220> FEATURE:
<223> OTHER INFORMATION: synthetic sequence

<400> SEQUENCE: 1

Gly Leu Leu Leu Leu Leu Lys Leu Leu Leu Leu Leu Leu Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: synthetic sequence

<400> SEQUENCE: 2

Gly Leu Leu Asp Leu Leu Lys Leu Leu Leu Lys Leu Leu Gly
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic sequence

<400> SEQUENCE: 3

Gly Leu Leu Asp Leu Leu Lys Leu Leu Leu Lys Ala Ala Gly
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic sequence

<400> SEQUENCE: 4

Gly Leu Leu Asp Leu Leu His Leu Leu Leu Lys Ala Ala Gly
1               5                   10

<210> SEQ ID NO 5
<211> LENGTH: 15
<212> TYPE: PRT
```

-continued

```
<213> ORGANISM: Artificial Sequence
<220> FEATURE:
<223> OTHER INFORMATION: synthetic sequence

<400> SEQUENCE: 5

Gly Leu Ala Asp Leu Ala Lys Leu Leu Leu Lys Leu Leu Gly Trp
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: synthetic sequence

<400> SEQUENCE: 6

Gly Leu Leu Asp Leu Leu Lys Leu Leu Leu Lys Leu Ala Gly Trp
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: synthetic sequence

<400> SEQUENCE: 7

Gly Leu Asp Asp Leu Ala Lys Leu Leu Leu Lys Leu Ala Gly Trp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic sequence

<400> SEQUENCE: 8

Gly Leu Asp Asp Leu Leu Lys Ala Leu Leu Lys Ala Ala Gly Trp
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic sequence

<400> SEQUENCE: 9

Gly Leu Leu Asp Asp Ala Lys Leu Leu Ala Lys Leu Ala Gly Trp
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: synthetic sequence

<400> SEQUENCE: 10

Gly Leu Leu Asp Leu Pro Lys Ala Leu Ala Lys Ala Leu Gly Trp
1               5                   10                  15

<210> SEQ ID NO 11
<211> LENGTH: 15
<212> TYPE: PRT
<213> ORGANISM: Artificial Sequence
```

<220> FEATURE:
<223> OTHER INFORMATION: synthetic sequence

<400> SEQUENCE: 11

Gly Leu Ala Asp Ala Ala Lys Leu Leu Leu Lys Ala Ala Gly Trp
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: synthetic sequence

<400> SEQUENCE: 12

Gly Leu Leu Asp Ala Ala Lys Leu Leu Ala Lys Ala Ala Gly Trp
1               5                   10                  15

<210> SEQ ID NO 13
<211> LENGTH: 20
<212> TYPE: PRT
<213> ORGANISM: Impatiens balsamina

<400> SEQUENCE: 13

Gln Tyr Gly Arg Arg Cys Cys Asn Trp Gly Pro Gly Arg Arg Tyr Cys
1               5                   10                  15

Lys Arg Trp Cys
            20

<210> SEQ ID NO 14
<211> LENGTH: 14
<212> TYPE: PRT
<213> ORGANISM: Hyla punctata

<400> SEQUENCE: 14

Gly Ile Leu Asp Ala Ile Lys Ala Ile Ala Lys Ala Ala Gly
1               5                   10

<210> SEQ ID NO 15
<211> LENGTH: 14
<212> TYPE: PRT
<213> ORGANISM: Hyla simplex

<400> SEQUENCE: 15

Gly Ile Leu Asp Pro Ile Lys Ala Phe Ala Lys Ala Ala Gly
1               5                   10

<210> SEQ ID NO 16
<211> LENGTH: 13
<212> TYPE: PRT
<213> ORGANISM: Artificial Sequence
<220> FEATURE:
<223> OTHER INFORMATION: synthetic sequence

<400> SEQUENCE: 16

Gly Leu Leu Ser Leu Leu Ser Leu Leu Gly Lys Leu Leu
1               5                   10

<210> SEQ ID NO 17
<211> LENGTH: 15
<212> TYPE: PRT
<213> ORGANISM: Litoria infrafrenata

<400> SEQUENCE: 17

Gly Leu Leu Gly Thr Leu Gly Asn Leu Leu Asn Gly Leu Gly Leu

<210> SEQ ID NO 18
<211> LENGTH: 13
<212> TYPE: PRT
<213> ORGANISM: Litoria aurea

<400> SEQUENCE: 18

Gly Leu Phe Asp Ile Ile Lys Lys Ile Ala Glu Ser Ile
1               5                   10

<210> SEQ ID NO 19
<211> LENGTH: 13
<212> TYPE: PRT
<213> ORGANISM: Litoria dahlii

<400> SEQUENCE: 19

Gly Leu Phe Asp Ile Ile Lys Asn Ile Val Ser Thr Leu
1               5                   10

<210> SEQ ID NO 20
<211> LENGTH: 16
<212> TYPE: PRT
<213> ORGANISM: Litoria fallax

<400> SEQUENCE: 20

Gly Leu Leu Asp Leu Ala Lys His Val Ile Gly Ile Ala Ser Lys Leu
1               5                   10                  15

<210> SEQ ID NO 21
<211> LENGTH: 13
<212> TYPE: PRT
<213> ORGANISM: Litoria ewingi

<400> SEQUENCE: 21

Gly Trp Phe Asp Val Val Lys His Ile Ala Ser Ala Val
1               5                   10

<210> SEQ ID NO 22
<211> LENGTH: 26
<212> TYPE: PRT
<213> ORGANISM: Apis mellifera

<400> SEQUENCE: 22

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 23
<211> LENGTH: 9
<212> TYPE: PRT
<213> ORGANISM: Apis mellifera

<400> SEQUENCE: 23

Gly Ile Gly Ala Val Leu Lys Val Leu
1               5

<210> SEQ ID NO 24
<211> LENGTH: 15
<212> TYPE: PRT
<213> ORGANISM: Artificial Sequence
<220> FEATURE:
<223> OTHER INFORMATION: synthetic sequence
<220> FEATURE:

```
<221> NAME/KEY: misc_feature
<222> LOCATION: (2)..(3)
<223> OTHER INFORMATION: Xaa is independently Ala, Leu, Lys, and Asp
<220> FEATURE:
<221> NAME/KEY: misc_feature
<222> LOCATION: (5)..(6)
<223> OTHER INFORMATION: Xaa is independently Ala, Leu, Lys, and Asp
<220> FEATURE:
<221> NAME/KEY: misc_feature
<222> LOCATION: (8)..(10)
<223> OTHER INFORMATION: Xaa is independently Ala, Leu, Lys, and Asp
<220> FEATURE:
<221> NAME/KEY: misc_feature
<222> LOCATION: (12)..(13)
<223> OTHER INFORMATION: Xaa is independently Ala, Leu, Lys, and Asp

<400> SEQUENCE: 24

Gly Xaa Xaa Asp Xaa Xaa Lys Xaa Xaa Xaa Lys Xaa Xaa Gly Trp
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: synthetic sequence

<400> SEQUENCE: 25

Lys Ile Ala Gly Lys Ile Ala
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic sequence

<400> SEQUENCE: 26

Gly Pro Ser Asn Asp Gln Glu Arg Lys
1               5

<210> SEQ ID NO 27
<211> LENGTH: 19
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (7)..(9)
<223> OTHER INFORMATION: Leu is either present or absent
<220> FEATURE:
<221> NAME/KEY: MISC_FEATURE
<222> LOCATION: (16)..(18)
<223> OTHER INFORMATION: Leu is either present or absent

<400> SEQUENCE: 27

Gly Leu Leu Leu Leu Leu Leu Leu Leu Arg Leu Leu Leu Leu Leu
1               5                   10                  15

Leu Leu Gly

<210> SEQ ID NO 28
<211> LENGTH: 13
<212> TYPE: PRT
<213> ORGANISM: Artificial Sequence
<220> FEATURE:
<223> OTHER INFORMATION: synthetic sequence

<400> SEQUENCE: 28
```

```
Gly Leu Leu Leu Leu Leu Arg Leu Leu Leu Leu Leu Gly
1               5                   10

<210> SEQ ID NO 29
<211> LENGTH: 15
<212> TYPE: PRT
<213> ORGANISM: Artificial Sequence
<220> FEATURE:
<223> OTHER INFORMATION: synthetic sequence

<400> SEQUENCE: 29

Gly Leu Leu Leu Leu Leu Leu Arg Leu Leu Leu Leu Leu Leu Gly
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (2)..(3)
<223> OTHER INFORMATION: Xaa is independently Gly, Ala, Val, Leu, Ile,
      Pro, Phe, Met, and Trp
<220> FEATURE:
<221> NAME/KEY: MISC_FEATURE
<222> LOCATION: (5)..(6)
<223> OTHER INFORMATION: Xaa is independently Gly, Ala, Val, Leu, Ile,
      Pro, Phe, Met, and Trp
<220> FEATURE:
<221> NAME/KEY: MISC_FEATURE
<222> LOCATION: (8)..(10)
<223> OTHER INFORMATION: Xaa is independently Gly, Ala, Val, Leu, Ile,
      Pro, Phe, Met, and Trp
<220> FEATURE:
<221> NAME/KEY: MISC_FEATURE
<222> LOCATION: (12)..(13)
<223> OTHER INFORMATION: Xaa is independently Gly, Ala, Val, Leu, Ile,
      Pro, Phe, Met, and Trp

<400> SEQUENCE: 30

Gly Xaa Xaa Asp Xaa Xaa Lys Xaa Xaa Xaa Lys Xaa Xaa Gly
1               5                   10
```